(12) United States Patent
Cho et al.

(10) Patent No.: US 6,731,984 B2
(45) Date of Patent: May 4, 2004

(54) METHOD FOR PROVIDING A THERAPY TO A PATIENT INVOLVING MODIFYING THE THERAPY AFTER DETECTING AN ONSET OF SLEEP IN THE PATIENT, AND IMPLANTABLE MEDICAL DEVICE EMBODYING SAME

(75) Inventors: Yong Kyun Cho, Maple Grove, MN (US); Donald N. Jensen, Derwood, MD (US); Luc R. Mongeon, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 215 days.

(21) Appl. No.: 09/876,528

(22) Filed: Jun. 7, 2001

(65) Prior Publication Data

US 2002/0193839 A1 Dec. 19, 2002

(51) Int. Cl.⁷ .............................................. A61N 1/365
(52) U.S. Cl. .......................................... 607/17; 607/20
(58) Field of Search ............................... 600/509, 513; 607/4–7, 9, 11, 17–20, 27

(56) References Cited

U.S. PATENT DOCUMENTS

| | | | |
|---|---|---|---|
| 3,941,135 A | 3/1976 | von Sturm et al. | 128/419 PS |
| 4,702,253 A | 10/1987 | Nappholz et al. | 128/419 PG |
| 4,711,245 A | 12/1987 | Higgins et al. | 128/635 |
| 4,795,542 A | 1/1989 | Ross et al. | 204/403 |
| 5,464,434 A * | 11/1995 | Alt | 607/6 |
| 5,476,483 A * | 12/1995 | Bornzin et al. | 607/17 |
| 5,562,711 A | 10/1996 | Yerich et al. | 607/17 |
| 5,622,428 A | 4/1997 | Bonnet | |
| 5,733,312 A | 3/1998 | Schloss et al. | 607/17 |
| 5,766,228 A | 6/1998 | Bonnet et al. | |
| 5,814,087 A * | 9/1998 | Renirie | 607/21 |
| 5,891,176 A | 4/1999 | Bornzin | 607/18 |
| 5,964,788 A | 10/1999 | Greenhut | 607/17 |
| 6,049,735 A | 4/2000 | Hartley et al. | 607/9 |
| 6,055,454 A | 4/2000 | Heemels | 607/18 |
| 6,122,536 A | 9/2000 | Sun et al. | 600/341 |
| 6,128,534 A * | 10/2000 | Park et al. | 607/17 |

* cited by examiner

Primary Examiner—Jeffrey R. Jastrzab
Assistant Examiner—Frances P. Oropeza
(74) Attorney, Agent, or Firm—Girma Wolde-Michael; Michael C. Seldner

(57) ABSTRACT

An implantable medical device system is described including an implantable medical device for implantation in a patient. One embodiment of the implantable medical device includes a therapy component for providing a therapy to the patient, a minute ventilation (MV) sensing circuit producing MV values indicative of a MV of the patient at time intervals, and computational circuitry. The computational circuitry receives a number of the MV values over a period of time, calculates a statistical parameter (e.g., a mean) of the MV values, and calculates a deviation of the MV values from the statistical parameter (e.g., a standard deviation of the MV values). The computational circuitry detects an onset of sleep in the patient when the deviation of the MV values from the statistical parameter is less than a predetermined MV threshold value, and signals the therapy component to modify the therapy when the onset of sleep is detected in the patient. A method is disclosed for providing therapy to a patient, including detecting an onset of sleep in the patient, and modifying the therapy following the detecting the onset of sleep in the patient.

48 Claims, 10 Drawing Sheets

METHOD FOR PROVIDING A THERAPY TO A PATIENT INVOLVING MODIFYING THE THERAPY AFTER DETECTING AN ONSET OF SLEEP IN THE PATIENT, AND IMPLANTABLE MEDICAL DEVICE EMBODYING SAME

BACKGROUND OF THE INVENTION

1. Field of the Invention

This invention relates generally to medical devices, and, more particularly, to implantable medical devices for providing various types of therapies to patients.

2. Description of the Related Art

A cardiac pacemaker (i.e., pacemaker) is an implantable medical device that delivers electrical stimulation (i.e., "pacing") pulses to cardiac tissue. Pacemakers are typically used to relieve symptoms associated with bradycardia, a condition in which patients cannot normally maintain physiologically acceptable heart rates. A wide variety of pacemakers are known and commercially available.

Early pacemakers delivered pacing pulses at regular intervals (i.e., constant rates) to maintain preselected heart rates. The preselected heart rate was typically deemed appropriate when the patient was at rest. Such pacemakers were known as "asynchronous" pacemakers because they did not synchronize pacing pulses with natural cardiac activity.

In contrast, the heart rate of a typical healthy person with a properly functioning heart increases during periods of elevated physical activity, and decreases during periods of reduced physical activity, to meet changing metabolic and physiologic needs. Accordingly, the metabolic and physiologic requirements of a patient receiving therapy via a pacemaker producing pacing pulses at a constant rate are typically not met when the patient is engaged in physical activity. During periods of elevated physical activity, the patient may experience adverse physiological consequences, including lightheadedness and/or episodes of fainting.

To reduce the adverse effects of constant rate pacing, "rate responsive" pacemakers have been developed that automatically adjust patients' heart rates to meet changing metabolic and physiologic demands. In a typical rate responsive pacemaker, the rate at which pacing pulses are produced (i.e., the "pacing rate") is variable between predetermined minimum and maximum rates. The minimum and maximum rates may be, for example, selected and programmed into the pacemaker by a physician. A "target" pacing rate of a rate responsive pacemaker may be expressed as:

Target Pacing Rate=Minimum Rate+$f$(sensor output)

where $f$ is a linear or monotonic function of an output of a single sensor, or the combined or "blended" outputs of multiple sensors.

Some known rate responsive pacemakers include only a single "activity" sensor (e.g., a piezoelectric crystal). In this situation, the rate response function $f$ is function of the activity sensor output. When the output of the activity sensor indicates that the patient's activity level has increased, the pacing rate is increased from the minimum rate by an incremental amount, which is determined as a function of the output of the activity sensor. As long as the activity sensor output indicates patient activity, the target pacing rate is periodically increased by incremental amounts calculated according to the above formula, until the maximum rate is reached. When patient activity ceases, the target pacing rate is gradually reduced, until the minimum rate is reached.

For any rate responsive pacemaker, it is desirable that the activity sensor output correlate to as high a degree as possible with the metabolic and physiologic needs of the patient, such that the pacing rate determined by the activity sensor output meets the metabolic and physiologic needs of the patient. It is noted that activity sensor output only indirectly represents a level of metabolic need. In addition, physical activity sensed by an activity sensor can be influenced by upper body motion. For example, an exercise involving arm motion may result in an activity sensor output corresponding to a relatively high level of metabolic need, while the actual level of metabolic need is much lower. Conversely, an exercise that stimulates the lower body only, such as bicycle riding, may result in an activity sensor output corresponding to a relatively low level of metabolic need, while the actual level of metabolic need is much higher.

Other known types of rate responsive pacemakers include multiple sensors, and the rate response function $f$ may be a function of an output of one or more of the multiple sensors at any given time. For example, a rate responsive pacemaker may include an activity sensor and a "minute ventilation sensor." Minute ventilation ($V_e$) is a parameter that has been demonstrated clinically to correlate directly to the actual metabolic and physiologic needs of a patient. Minute ventilation may be defined by the equation:

$$V_e = RR \times VT$$

where RR is a "respiration rate" in breaths per minute, and VT is a "tidal volume" of each breath in liters. Clinically, the measurement of $V_e$ is performed by having the patient breathe directly into a device that measures the exchange of air and computes the total volume per minute.

While it is not possible for an implanted device, such as a pacemaker, to directly measure minute ventilation, it is possible for such an implanted device to measure impedance changes in the thoracic cavity. It is well known that a change in thoracic impedance corresponds to a change in tidal volume (VT), and a frequency of such changes over time corresponds to respiration rate (RR). (See, for example, U.S. Pat. No. 4,702,253 issued to Nappholz et al. on Oct. 27, 1987.) In a rate responsive pacemaker, circuitry configured to measure thoracic impedance, to extract respiratory rate (RR) and tidal volume (VT) values from thoracic impedance measurements, and to produce an output that represents a product of the respiratory rate (RR) and tidal volume (VT) values may be considered a "minute ventilation sensor."

Both respiration rate (RR) and tidal volume (VT) have inherent physiologic time delays due to the response of $CO_2$ receptors and the autonomic nervous system. As a result, an increase in minute ventilation ($V_e$) occurs after the onset of exercise and lags behind a need for increased cardiac output.

In rate responsive pacemakers having multiple sensors, rate response function $f$ may be selected such that the pacing rate is based on the combined or "blended" outputs of the multiple sensors. For example, known rate responsive pacemakers include an activity sensor and a "minute ventilation sensor" as described above. In such rate responsive pacemakers, the rate response function $f$ may be selected such that the pacing rate is based substantially (or even solely) on the activity sensor output when the patient is relatively inactive, and based substantially on the output of the "minute ventilation sensor" when the patient is relatively active.

Human sleep-wake cycles are examples of biological rhythms called "circadian rhythms"—internally originating cycles of behavior or biological activity with a period of about 24 hours. It is believed that human sleep-wake cycles are generated by an internal clock that is synchronized to light-dark cycles in the environment and other daily cues.

While the typical healthy person with a properly functioning heart is awake but relatively inactive, the person's heart rate is usually at a "resting rate." When the person is sleeping, the person's heart rate typically drops to a "sleeping rate" that is less than the resting rate. On the other hand, the heart rate of a patient receiving therapy via a typical rate responsive pacemaker is maintained at the above described minimum rate when the patient is both awake but relatively inactive and sleeping. While the difference between the "resting rate" and the "sleeping rate" may be relatively small (e.g., about 5 beats per minute), the inability of the typical pacemaker to reduce the patient's heart rate when the patient is sleeping may cause the patient to have difficulty falling asleep and/or sleeping well. In addition, since it is likely that the patient could tolerate, and even benefit from, a lower heart rate while sleeping, the pacemaker may be viewed as wasting limited energy reserves by maintaining the unnecessarily high minimum rate while the patient is sleeping.

Pacemakers are known that include an internal clock for keeping track of time and having a "sleep time" function, wherein when the "sleep time" function is enabled, the above described "target" heart rate for a patient receiving therapy via the pacemaker is reduced to a "sleep rate," which is typically lower than the programmed "minimum rate," during a "sleep period" between a programmable "bed time" and a programmable "wake time." A problem arises, however, in that the above timekeeping method is not optimal when the patient changes his/her bed time and/or wake time, travels to a different time zone, etc.

The present invention is directed to a method that may solve, or at least reduce, some or all of the aforementioned problems, and systems incorporating the method.

SUMMARY OF THE INVENTION

An implantable medical device system is described including an implantable medical device for implantation in a patient. One embodiment of the implantable medical device includes a therapy component, a minute ventilation sensing circuit, and computational circuitry coupled to the therapy component and the minute ventilation sensing circuit. The therapy component provides a therapy to the patient. The minute ventilation sensing circuit produces minute ventilation values indicative of a minute ventilation of the patient at time intervals. The computational circuitry receives a number of the minute ventilation values over a period of time, calculates a central tendency (e.g., a mean) of the minute ventilation values, and calculates a deviation of the minute ventilation values from the central tendency (e.g., a standard deviation of the minute ventilation values). The computational circuitry detects an onset of sleep in the patient when the deviation of the minute ventilation values from the central tendency is less than a predetermined minute ventilation threshold value, and signals the therapy component to modify the therapy when the onset of sleep is detected in the patient. For example, where the computational circuitry calculates a standard deviation of the minute ventilation values, the computational circuitry may detect the onset of sleep in the patient when the standard deviation of the minute ventilation values is less than the minute ventilation threshold value.

The implantable medical device may also include an activity sensing circuit producing activity values indicative of an activity level of the patient at time intervals, and the computational circuitry may be coupled to receive the activity values. The computational circuitry may detect the onset of sleep in the patient when: (i) the deviation of the minute ventilation values from the central tendency is less than the predetermined minute ventilation threshold value, and (ii) an activity value indicative of a current level of activity of the patient is less than an activity threshold value.

Further, the computational circuitry may be configured to keep track of a time of day. The computational circuitry may detect the onset of sleep in the patient when: (i) the deviation of the minute ventilation values from the central tendency is less than the predetermined minute ventilation threshold value, and (ii) an activity value indicative of a current level of activity of the patient is less than an activity threshold value, and (iii) a current time of day is greater than or equal to an expected sleep time value, wherein the expected sleep time value is indicative of a time of day the patient is expected to go to sleep.

The implantable medical device may be, for example, an implantable pacemaker, and the therapy component may be a pacing output unit of the pacemaker. The pacing output unit may be configurable to provide electrical stimulation to a portion of a heart of the patient dependent upon a low rate limit value, wherein the low rate limit value specifies a minimum rate of sensed contractions of the portion of the heart. The computational circuitry may detect an onset of sleep in the patient as described above, and may reduce the low rate limit value when the onset of sleep is detected in the patient.

A method is disclosed for providing therapy to a patient, including detecting an onset of sleep in the patient, and modifying the therapy following the detecting the onset of sleep in the patient. In one embodiment, detection of the onset of sleep includes: (i) receiving multiple minute ventilation values over a period of time, wherein the minute ventilation values are indicative of a minute ventilation of the patient, (ii) calculating a central tendency of the minute ventilation values, (iii) calculating a deviation of the minute ventilation values from the central tendency, and (iv) detecting the onset of sleep in the patient if the deviation of the minute ventilation values from the central tendency is less than a predetermined minute ventilation threshold value.

As described above, the calculation of the central tendency may include calculating a mean of the minute ventilation values, and the calculating the deviation of the minute ventilation values from the central tendency may include calculating a standard deviation of the minute ventilation values. The onset of sleep may be detected in the patient if the standard deviation is less than the minute ventilation threshold value.

The method may also include receiving an activity value indicative of a current level of activity of the patient. In this situation, the onset of sleep may be detected in the patient if: (i) the deviation of the minute ventilation values from the central tendency is less than the predetermined minute ventilation threshold value, and (ii) the activity value is less than an activity threshold value. Alternately, onset of sleep may be detected in the patient if: (i) the deviation of the minute ventilation values from the central tendency is less than the predetermined minute ventilation threshold value, and (ii) the activity value is less than the activity threshold value, and (iii) a current time of day is greater than or equal to an expected sleep time, wherein the expected sleep time is a time of day the patient is expected to go to sleep.

In one embodiment of the method, the detecting the onset of sleep in the patient involves receiving a first number of the minute ventilation values over a first period of time. The first period of time may be, for example, greater than or equal to 24 hours. The first number of the minute ventilation values is used to determine a minute ventilation threshold value. A second number of the multiple minute ventilation values are received over a second period of time following the first period of time. A central tendency of the second number of minute ventilation values is calculated, as is a deviation of the second number of minute ventilation values from the central tendency. The onset of sleep is detected in the patient if the deviation of the second number of minute ventilation values from the central tendency is less than the minute ventilation threshold value.

The using the first number of minute ventilation values to determine the minute ventilation threshold value may include, for example, receiving a portion of the first number of minute ventilation values during each of multiple time intervals of the first period of time. At the end of each time interval, the following may be calculated: (i) a central tendency of the minute ventilation values received during the time interval, and (ii) a deviation of the minute ventilation values received during the time interval from the central tendency. A histogram may be formed reflecting the deviations of the minute ventilation values received during the time intervals from the central tendencies. A pair of peaks may be located in the histogram. A minute ventilation value residing between the peaks in the histogram may be selected as the minute ventilation threshold value.

For example, at the end of each time interval, the following may be calculated: (i) a mean of the minute ventilation values received during the time interval, and (iii) a standard deviation of the minute ventilation values received during the time interval. In this situation, the histogram reflects the standard deviations of the minute ventilation values received during the time intervals.

BRIEF DESCRIPTION OF THE DRAWINGS

The invention may be understood by reference to the following description taken in conjunction with the accompanying drawings, in which like reference numerals identify similar elements, and in which.

Figure 1:
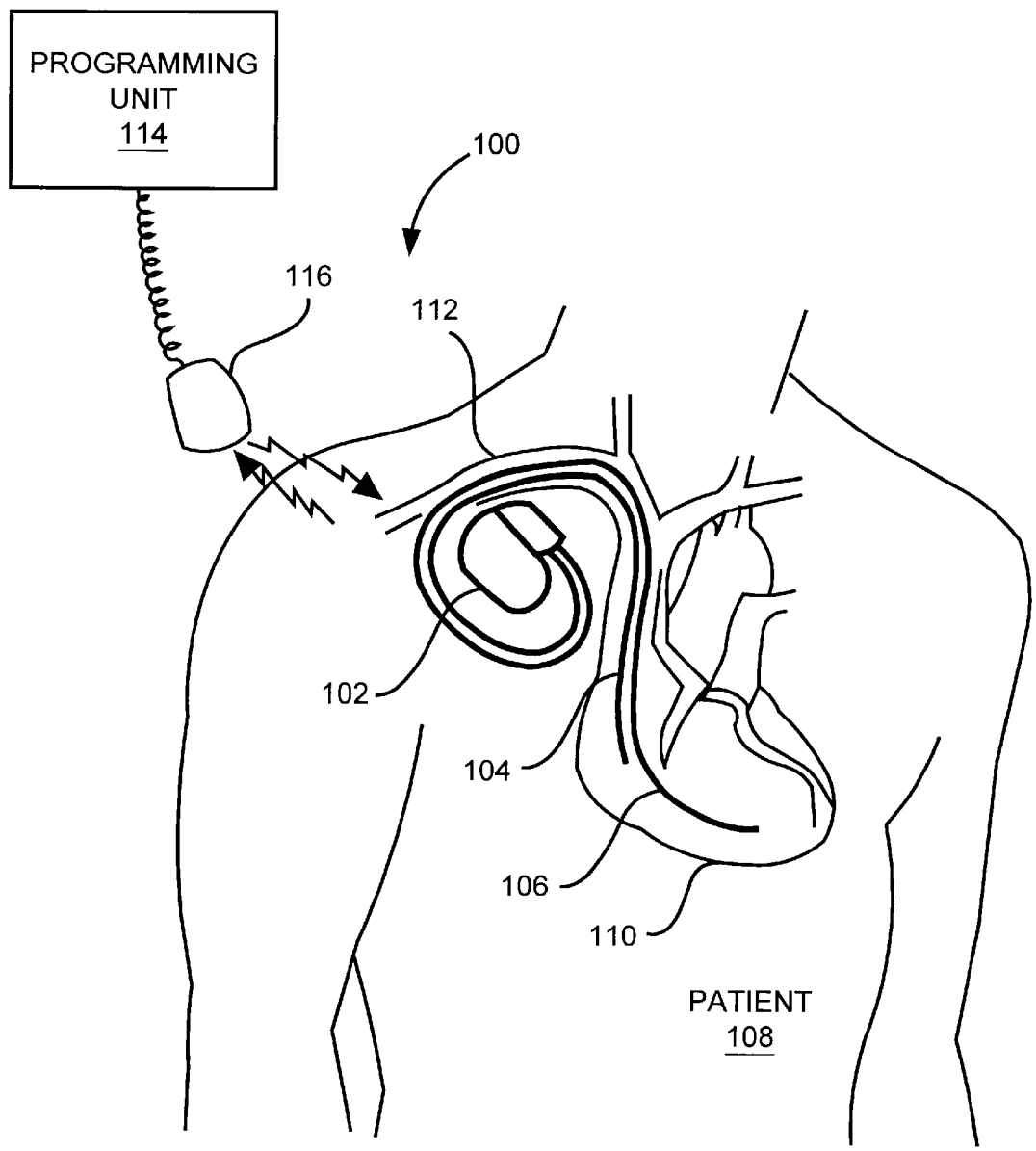
FIG. 1 is a diagram of one embodiment of an implantable medical device (IMD) system including a cardiac pacemaker, an atrial lead, and a ventricular lead implanted in a patient.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will, of course, be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

FIG. 1 is a diagram of one embodiment of an implantable medical device (IMD) system 100 including a cardiac pacemaker 102, an atrial lead 104, and a ventricular lead 106 implanted in a patient 108. The pacemaker 102 produces electrical pulses (i.e., pacing pulses) that stimulate a heart 110 of the patient 108. One end of the atrial lead 104 is electrically coupled to the pacemaker 102, the other end of the atrial lead 104 extends through a vein 112 into a right atrium of the heart 110. One end of the ventricular lead 106 is electrically coupled to the pacemaker 102, the other end of the ventricular lead 106 extends through the vein 112 and into a right ventricle of the heart 110. Electrically conductive electrodes attached to the ends of the atrial lead 104 and the ventricular lead 106 located within the heart 110 are used to deliver pacing pulses to the heart 110, and to receive intrinsic electrical signals present within the heart 110.

The pacemaker 102 may be housed within a hermetically sealed, biologically inert outer canister or housing. At least a portion of the housing may be electrically conductive, and may serve as an electrode in pacing and/or sensing circuits of the pacemaker 102.

The IMD system 100 of FIG. 1 also includes a programming unit 114 for programming the pacemaker 102. A programming head 116 is connected to the programming unit 114, and enables two-way communication between the programming unit 114 and the pacemaker 102 as indicated in FIG. 1. For example, the programming head 116 may include a radio frequency (RF) antenna, and may send RF signals to, and receive RF signals from, the pacemaker 102.

Figure 2:
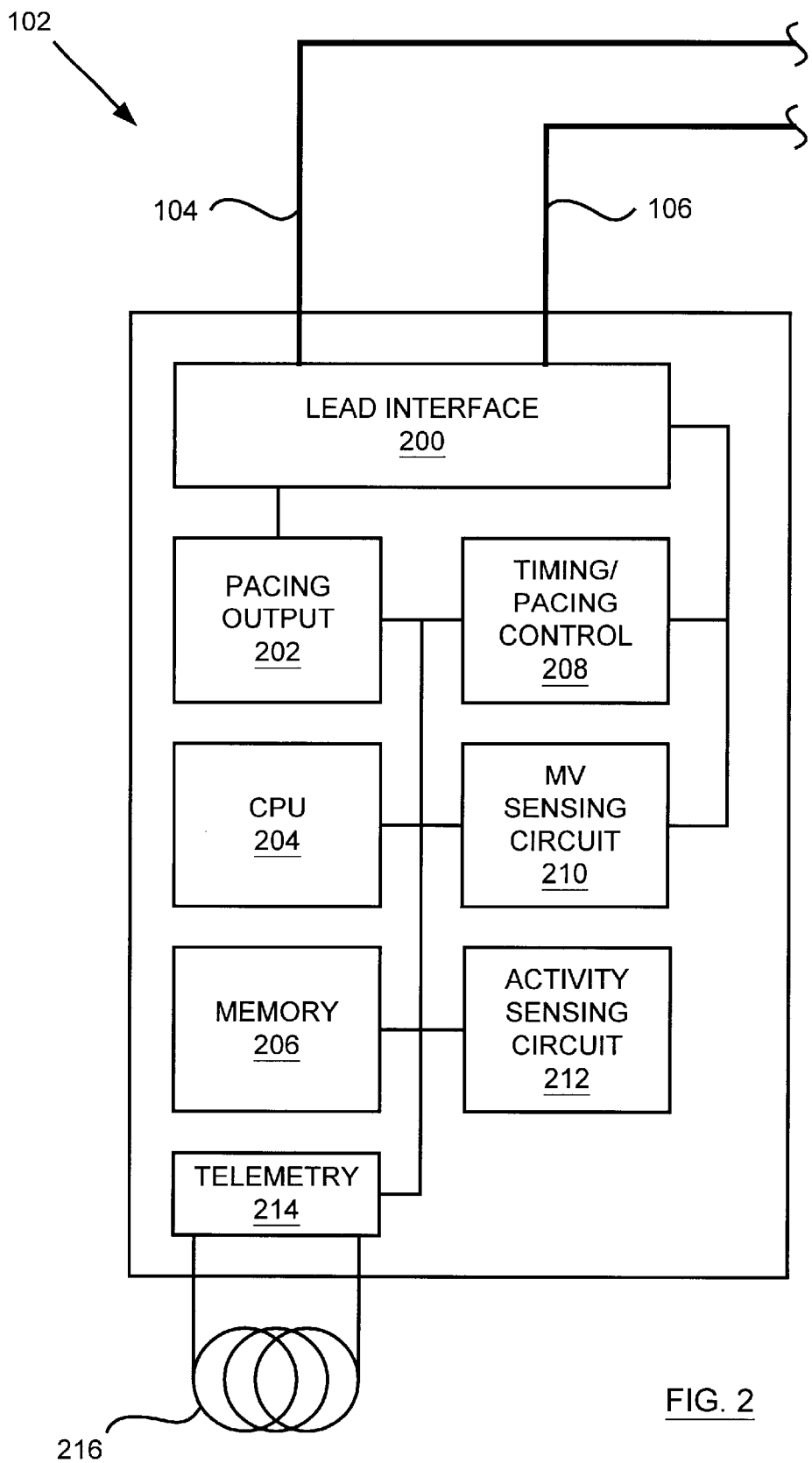
FIG. 2 is a diagram of one embodiment of the cardiac pacemaker of FIG. 1, wherein the pacemaker produces pacing pulses delivered to a heart of the patient of FIG. 1 via the atrial lead and the ventricular lead.
Figure 3A:
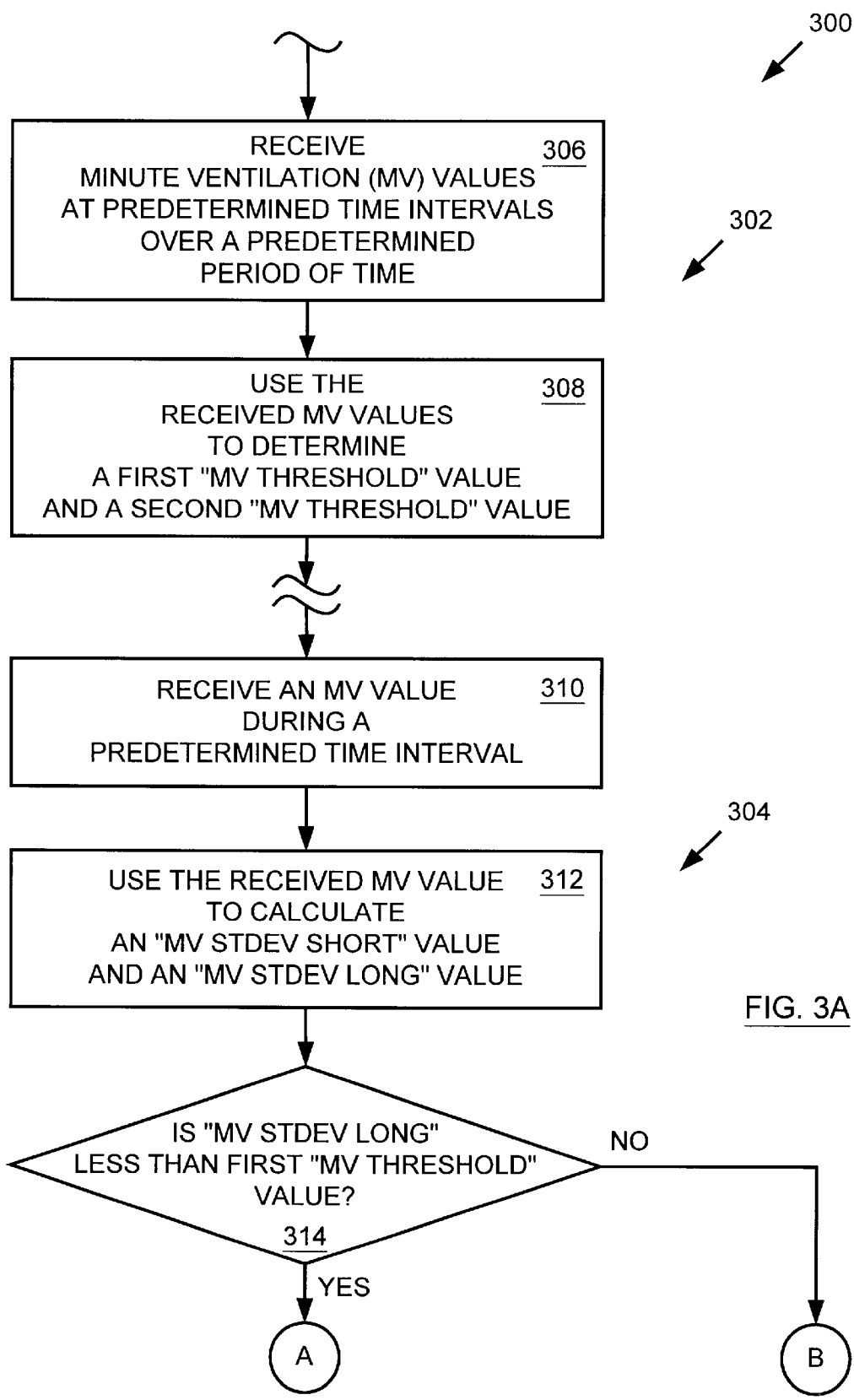
FIGS. 3A–3D in combination form a flow chart of one embodiment of a method for determining an onset of sleep in a patient having an implantable medical device (e.g., the pacemaker of FIGS. 1–2) implanted therein.
Figure 3B:
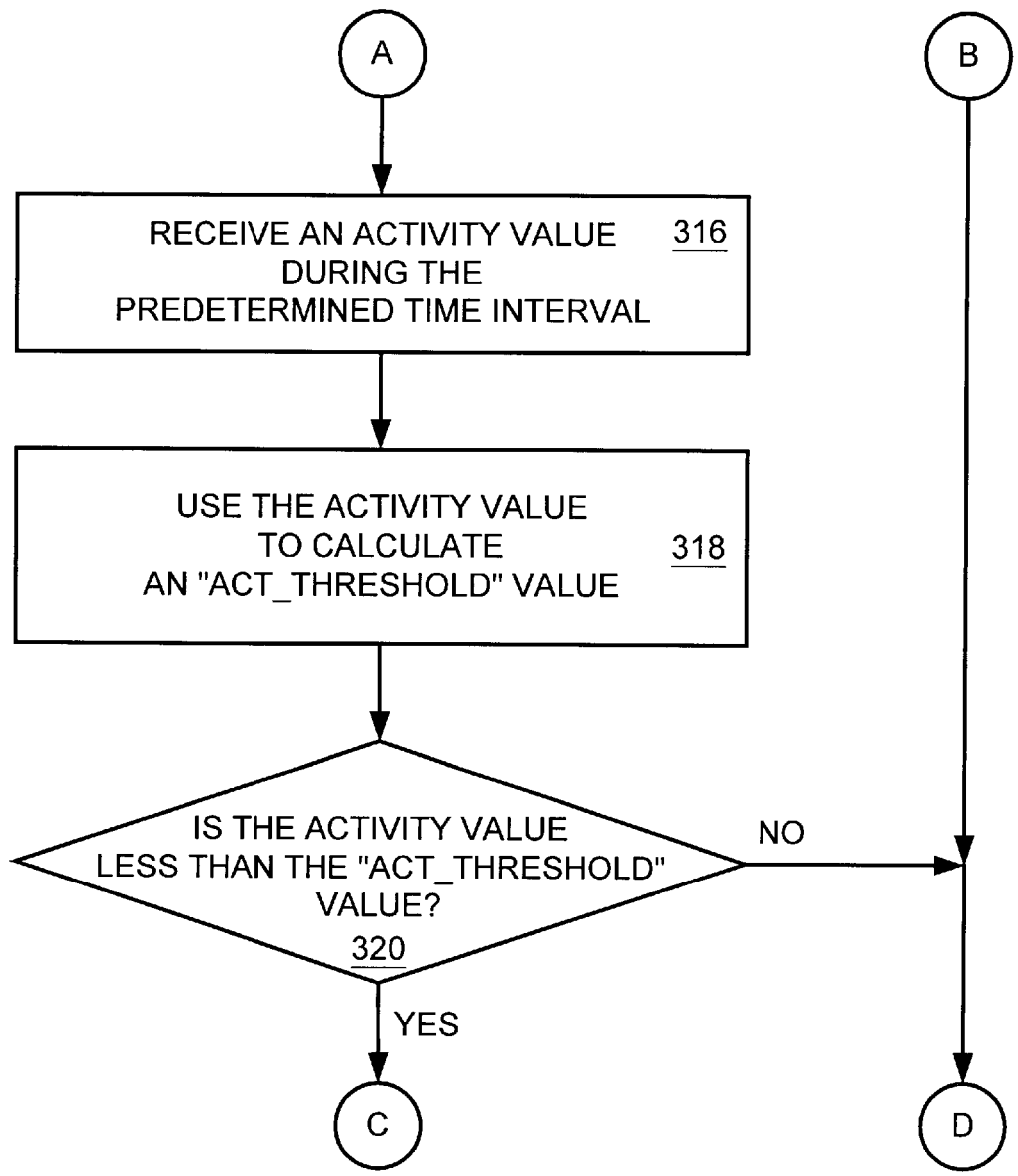
Figure 3C:
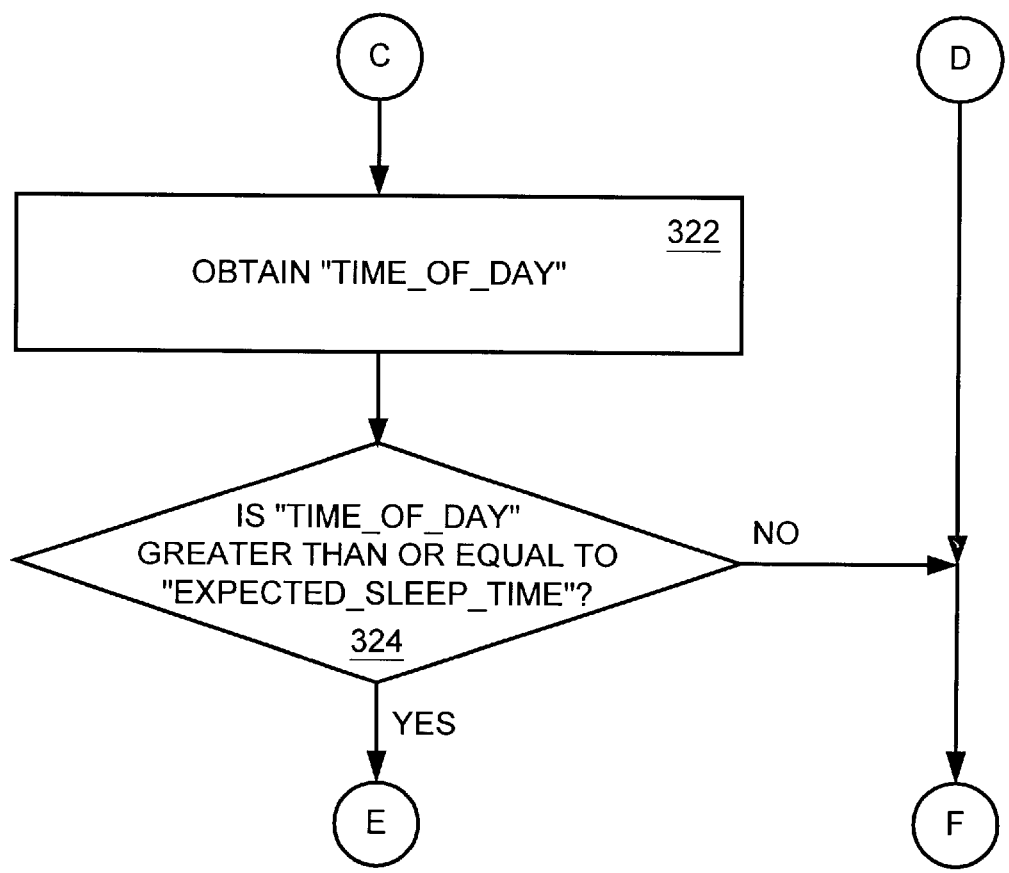
Figure 3D:
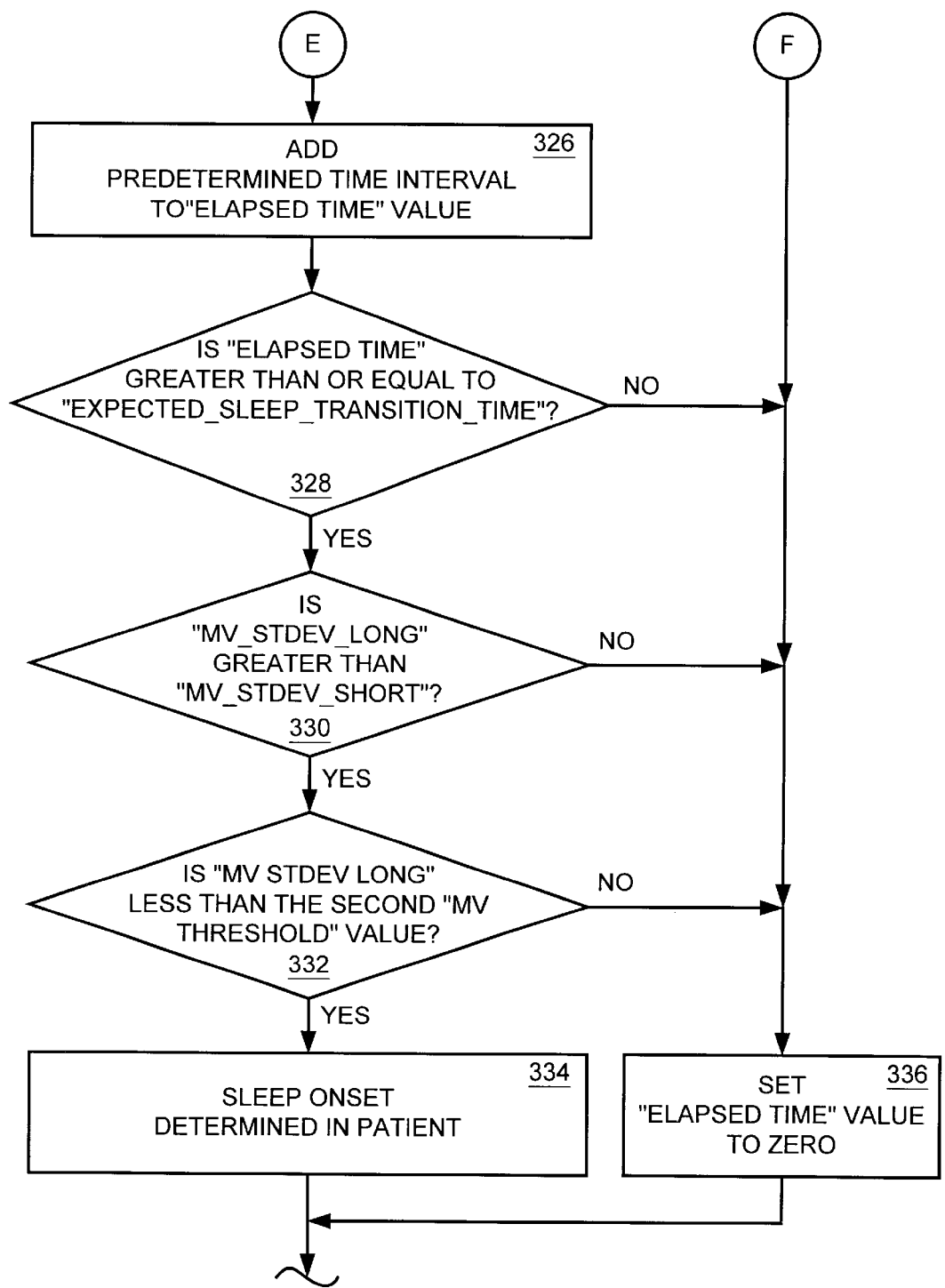

FIG. 2 is a diagram of one embodiment of the cardiac pacemaker 102 of FIG. 1. As described above, the pacemaker 102 produces pacing pulses delivered to the heart 110 of the patient 108 (FIG. 1) via the atrial lead 104 and the ventricular lead 106. In the embodiment of FIG. 2, the pacemaker 102 includes lead interface circuitry 200, pacing output circuitry 202, a central processing unit (CPU) 204, a memory 206, timing/pacing control circuitry 208, a minute ventilation (MV) sensing circuit 210, an activity sensing circuit 212, a telemetry unit 214, and an antenna 216.

The atrial lead 104 and the ventricular lead 106 conduct pacing pulses produced by the pacemaker 102 to the heart 110 of the patient 108 (FIG. 1), and also conduct intrinsic electrical signals present within the heart 110 to the pacemaker 102. The lead interface circuitry 200 forms an electrical interface between the atrial lead 104 and the ventricular lead 106 and other components of the pacemaker 102. As will be described in detail below, the pacing output circuitry 202 produces atrial and ventricular pacing pulses for stimulating the heart 110. The CPU 204 executes instructions stored in the memory 206, and controls the operations of other components of the pacemaker 102.

Adapted for connecting to the atrial lead 104 and the ventricular lead 106 and capable of delivering pacing pulses to the right atrium and the right ventricle of the heart 110 (FIG. 1), the pacemaker 102 of FIGS. 1 and 2 may be termed a "dual-chamber" pacemaker. The pacemaker 102 may be programmable to operate in one or more of several different predefined operating modes, including a "demand" mode. In the "demand mode," the pacemaker 102 senses intrinsic electrical signals present within the heart 110 of the patient 108 (FIG. 1), and produces pacing pulses only when the pacing pulses are needed. For example, the pacemaker 102 may be programmed with a value indicating whether or not the "demand" mode is enabled, a "low rate limit" value indicating a low limit of an intrinsic beat rate of the heart 110 of the patient 108 (FIG. 1), and an "atrioventricular (AV) interval" value indicating a maximum length of time between an atrial contraction or "atrial beat" and a subsequent ventricular contraction or "ventricular beat."

The timing/pacing control circuitry 208 may include various registers for storing values indicative of programmed parameters of the pacemaker 102, and various counters for performing timing functions. For example, the CPU 204 may store programmed "demand" mode, "low rate limit," and "AV interval" values in one or more registers of the timing/pacing control circuitry 208.

The timing/pacing control circuitry 208 includes sensing circuitry that receives and detects intrinsic electrical signals present within the heart 110 of the patient 108 (FIG. 1). Specifically, the sensing circuitry of the timing/pacing control circuitry 208 receives a first electrical signal indicative of an intrinsic contraction of the right atrium via the atrial lead 104. In response the first electrical signal, the sensing circuitry may generate an "atrial beat" signal within the timing/pacing control circuitry 208.

If the "demand" mode of the pacemaker 102 is enabled, the timing/pacing control circuitry 208 may provide an "atrial trigger" signal to the pacing output circuitry 202 if a frequency at which the "atrial beat" signals are generated is below the programmed "low rate limit." In other words, the timing/pacing control circuitry 208 may provide an "atrial trigger" signal to the pacing output circuitry 202 if the intrinsic beat rate of the heart 110 (FIG. 1) falls below the programmed "low rate limit." In response to the atrial trigger signal, the pacing output circuitry 202 may produce an atrial pacing pulse, and provide the atrial pacing pulse to the right atrium of the heart 110 (FIG. 1) via the atrial lead 104. The atrial pacing pulse typically causes the right and left atria of the heart 110 to contract in unison.

The sensing circuitry of the timing/pacing control circuitry 208 also receives a second electrical signal indicative of an intrinsic contraction of the right ventricle via the ventricular lead 106. In response the second electrical signal, the sensing circuitry may generate a "ventricular beat" signal within the timing/pacing control circuitry 208. If the "demand" mode of the pacemaker 102 is enabled and the "ventricular beat" signal is not generated within the programmed "AV interval" following an "atrial beat" signal, the timing/pacing control circuitry 208 may provide a "ventricular trigger" signal to the pacing output circuitry 202. In response to the "ventricular trigger" signal, the pacing output circuitry 202 may produce a ventricular pacing pulse, and provide the ventricular pacing pulse to the right ventricle of the heart 110 (FIG. 1) via the ventricular lead 106. The ventricular pacing pulse typically causes the right and left ventricles of the heart 110 to contract in unison.

The minute ventilation sensing circuit 210 produces a minute ventilation output signal indicative of the minute ventilation of the patient 108 (FIG. 1). In one embodiment, the minute ventilation sensing circuit 210 produces the minute ventilation output signal dependent upon changes of electrical impedance in a thoracic cavity of the patient 108, and the minute ventilation output signal constitutes digital values indicative of the minute ventilation of the patient 108 produced at regular time intervals. In other embodiments, the minute ventilation output signal may be a continuous analog signal.

As described above, electrically conductive electrodes are attached to the ends of the atrial lead 104 and the ventricular lead 106 (FIG. 1), and at least a portion of the outer canister or housing of the pacemaker 102 (FIGS. 1–2) may be electrically conductive. The minute ventilation sensing circuit 210 may deliver an electrical current excitation signal between a first electrode, at the end of either the atrial lead 104 or the ventricular lead 106, and the outer canister or housing of the pacemaker 102. The current excitation signal may include, for example, current pulses delivered at a predetermined rate (e.g., 16 pulses per second, or 16 Hertz). An electrical voltage signal may be measured between a second electrodes, at the end of the atrial lead 104 or the ventricular lead 106, and the outer canister or housing of the pacemaker 102. A thoracic impedance signal may be generated by dividing a magnitude of the electrical voltage signal by a magnitude of the electrical current excitation signal.

The thoracic impedance signal is a voltage signal having three main components: a direct current (d.c.) offset voltage, a cardiac component resulting from the function of the heart 110 of the patient 108 (FIG. 1), and a respiratory component. The minute ventilation sensing circuit 210 may include, for example, a bandpass filter (e.g., having a passband of, for example, 0.05 Hz to 0.8 Hz), and the thoracic impedance signal may be passed through the bandpass filter to substantially remove the d.c. offset voltage and the cardiac component. The resulting "filtered" thoracic impedance signal, emerging at an output of the bandpass filter, substantially comprises the respiratory component.

The minute ventilation sensing circuit 210 may also include sample-and-hold circuitry and comparison circuitry (not shown). As described above, the minute ventilation sensing circuit 210 may deliver current pulses at a predetermined rate (e.g., 16 Hz). The predetermined rate defines a time interval between pulses, referred to herein as a "cycle time." At the beginning of each cycle time, the minute ventilation sensing circuit 210 delivers a current pulse. The sample-and-hold circuitry may sample the filtered thoracic impedance signal at the beginning of each cycle time, thereby acquiring a "current" value of the filtered thoracic impedance signal. The comparison circuitry may compare the "current" value of the filtered thoracic impedance signal to a "previous" value of the filtered thoracic impedance signal, acquired by the sample-and-hold circuitry at the beginning of the preceding cycle time. The comparison circuitry may produce an analog "difference" voltage equal to a difference between the "current" value of the filtered thoracic impedance signal and the "previous" value of the thoracic impedance signal.

The minute ventilation sensing circuit 210 may also include analog-to-digital conversion circuitry, summing circuitry, and a register (not shown). The analog-to-digital conversion circuitry may convert the analog difference voltage produced by the comparison circuitry to a digital "count" value representing the difference between the "current" value of the filtered thoracic impedance signal and the "previous" value of the thoracic impedance signal at the beginning of the preceding cycle time. The summing circuitry may sum the digital "count" values produced by the analog-to-digital conversion circuitry over a predetermined number of the cycle times (i.e., over a predetermined time interval). The resulting sum of the digital "count" values, acquired over the predetermined time interval, is referred to herein as a "minute ventilation count value." A digital "minute ventilation count value" is thus present in the register at the end of each predetermined time interval, wherein the digital "minute ventilation count value" is indicative of the minute ventilation of the patient 108 (FIG. 1). At the end of each predetermined time interval, the digital "minute ventilation count value" (i.e., the contents of the register) may be provided to the CPU 204 (e.g., via an interrupt or programmed input/output mechanism), and the register may be cleared.

For example, the minute ventilation sensing circuit 210 may deliver current pulses at a rate of 16 Hz as described above. The summing circuitry may sum 32 of the digital "count" values produced by the analog-to-digital conversion circuitry over a predetermined 2-second time interval. At the end of each 2-second time interval, the digital "minute ventilation count value" (i.e., the contents of the register) may be provided to the CPU 204 (e.g., via an interrupt or programmed input/output mechanism), and the register may be cleared.

It is noted that there are several known methods for producing measures of minute ventilation of the patient 108 (FIG. 1), any one of which may be employed by the minute ventilation sensing circuit 210 to produce the minute ventilation output. For example, in other contemplated embodiments, the minute ventilation output may be a continuous analog waveform indicative of the minute ventilation of the patient 108 (FIG. 1). The continuous analog waveform may be sampled at regular intervals, and the analog samples may be converted to corresponding digital values.

The activity sensing circuit 212 senses movement or physical activity of the patient 108 (FIG. 1), and produces an "activity output" indicative of a magnitude of the movement or physical activity of the patient 108. In one embodiment, the "activity output" constitutes digital "activity values" produced at regular time intervals. In other embodiments, the "activity output" may be a continuous analog signal.

The activity sensing circuit 212 may include, for example, an element producing an electrical signal when subjected to mechanical stress (e.g., a piezoelectric crystal), and a mechanical apparatus for subjecting the element to mechanical stress when the patient 108 moves or is physically active. The element and the mechanical apparatus for subjecting the element to mechanical stress when the patient 108 moves or is physically active may form, for example, an accelerometer (not shown). The accelerometer may produce an output signal. Alternately, the activity sensing circuit 212 may include a piezoelectric sensor bonded to an inner surface of the outer canister or housing of the pacemaker 102 (FIGS. 1–2), and the piezoelectric sensor may produce the output signal.

The activity sensing circuit 212 may include a bandpass filter, and the output signal of the accelerometer or piezoelectric sensor may be coupled to an input of the bandpass filter. An output signal produced by the bandpass filter may be compared to a threshold value (e.g., a programmable threshold value). Peaks in the output signal of the bandpass filter which exceed the threshold value, referred to herein as "activity counts," may indicate movement or physical activity of the patient 108 (FIG. 1) of sufficient magnitude that an increase in pacing rate may be warranted.

The activity sensing circuit 212 may include circuitry for summing "activity counts" occurring within predetermined time intervals (e.g., two second time intervals), and a register for storing the sum of the "activity counts." At the end of each regular time interval, the corresponding sum of the "activity counts," contained within the register, constitutes a digital "activity value." The contents of the register may be provided to the CPU 204 at the end of each regular time interval (e.g., via an interrupt or programmed input/output mechanism), and the register may be cleared.

It is noted that there are several known methods for producing measures of movement or physical activity of the patient 108 (FIG. 1), any one of which may be employed by the activity sensing circuit 212 to produce the "activity output."

The pacemaker 102 is typically programmed with a "high rate limit" value indicating a high limit of an intrinsic beat rate of the heart 110 of the patient 108. If a "rate response" mode of the pacemaker 102 is enabled (e.g., via a programmable parameter), the CPU 204 may execute software instructions stored in the memory 206 that implement the "rate response" mode.

In this situation, the CPU 204 may vary the "low rate limit" value and/or the "AV interval" value stored in the timing/pacing control circuitry 208, dependent upon the minute ventilation output produced by the MV sensing circuit 210 and/or the activity output produced by the activity sensing circuit 212. the CPU 204 may vary the "low rate limit" value and/or the "AV interval" value according to a transfer function (e.g., a programmable transfer function) to achieve a rate response defined by the "low rate limit" value, the "high rate limit" value, and the transfer function. As a result, the rate at which the pacing output circuitry 202 produces the atrial pacing pulses is varied between the "low rate limit" and the "high rate limit" dependent upon the minute ventilation output produced by the MV sensing circuit 210 and/or the activity output produced by the activity sensing circuit 212. For example, a "target" pacing rate at which pacing output circuitry 202 produces the atrial pacing pulses may be expressed as:

"target"pacing rate="low rate limit"+$f$(sensing circuit output)

where $f$ is a linear or monotonic function of the minute ventilation output produced by the MV sensing circuit 210 and/or the activity output produced by the activity sensing circuit 212.

For example, when the activity output produced by the activity sensing circuit 212 indicates that an activity level of the patient 108 (FIG. 1) has increased, the "target" pacing rate may be increased from the "low rate limit" by incremental amounts determined by the activity output produced by the activity sensing circuit 212. As long as the activity output produced by the activity sensing circuit 212 indicates activity of the patient 108, the "target" pacing rate may be periodically increased by incremental amounts until the "high rate limit" is reached. When the activity output produced by the activity sensing circuit 212 indicates activity of the patient 108 has ceased, the "target" pacing rate may be gradually reduced by incremental amounts until the "low rate limit" is reached.

The rate response function $f$ is preferably selected such that the "target" pacing rate is based on a combination of the outputs of the activity sensing circuit 212 and the minute ventilation sensing circuit 210. For example, the rate response function $f$ may be selected such that the "target" pacing rate is based substantially on the activity output produced by the activity sensing circuit 212 when the patient is relatively inactive, and based substantially on the minute ventilation output produced by the minute ventilation sensing circuit 210 when the patient is relatively active. Any one of several known methods for combining or "blending" outputs of activity sensors and minute ventilation sensors may be employed in generating the "target" pacing rate.

The telemetry unit 214 is coupled to the antenna 216, and communicates with the programming head 116 (FIG. 1) via antenna 216. For example, the antenna 216 may be a radio frequency (RF) antenna, and the telemetry unit 214 may send RF signals to, and receive RF signals from, the programming head 116 (FIG. 1). In the embodiment of FIGS. 1 and 2, CPU 204 communicates with the programming unit 114 (FIG. 1) via the telemetry unit 214, the antenna 216, and the programming head 116. CPU 204 receives values to be stored in memory locations of the memory 206 from the programming unit 114 via the telemetry unit 214. The received values may be, for example, the values of programmable parameters, which determine the operation of the pacemaker 102. CPU 204 may also use the telemetry unit 214 to transmit values residing in memory locations of the memory 206 to the programming unit 114. The transmitted values may be, for example, the values of programmable parameters, which determine the operation of the pacemaker 102, and/or data indicative of sensed parameters of the patient 108 (FIG. 1).

FIGS. 3A–3D in combination form a flow chart of one embodiment of a method 300 for determining an onset of sleep in a patient (e.g., patient 108 of FIG. 1) having an implantable medical device (e.g., pacemaker 102 of FIGS. 1–2) implanted therein. The method 300 may be embodied within software residing in the memory 206 (FIG. 2) of the pacemaker 102. The CPU 204 (FIG. 2) may carry out the method 300 when executing the software embodying the method 300.

The method 300 includes a "preliminary" portion 302 and a "recurrent" portion 304. During the preliminary portion 302, two minute ventilation threshold values are determined. At least some of the steps of the recurrent portion 304 are carried out at predetermined time intervals. The minute ventilation threshold values determined during the preliminary portion 302 are used during the recurrent portion 304 to determine the onset of sleep in a patient having the implantable medical device implanted therein.

During a step 306 of the preliminary portion 302, "minute ventilation values" are received at predetermined time intervals over a predetermined period of time. The minute ventilation values are indicative of the minute ventilation of the patient having the implantable medical device implanted therein. For example, in one embodiment of the minute ventilation sensing circuit 210 (FIG. 2) described above, the minute ventilation sensing circuit 210 delivers current pulses at a rate of 16 Hz, thereby defining pulse "cycles" having "cycle times" of $\frac{1}{16}$ or 0.0625 seconds. The minute ventilation sensing circuit 210 converts an analog difference voltage between a "current" value of a thoracic impedance signal, obtained during a "current" pulse cycle, and a "previous" value of the thoracic impedance signal, obtained during a pulse cycle preceding the current pulse cycle, to a digital "count" value. The minute ventilation sensing circuit 210 sums 32 of the digital "count" values produced by the analog-to-digital conversion circuitry in a register over a predefined 2-second time interval. The minute ventilation sensing circuit 210 provides a "minute ventilation value" contained in the register at the end of each 2-second time interval, then clears the register.

During a second step 308 of the preliminary portion 302, the minute ventilation values received during the step 306 are used to determine a first minute ventilation threshold value and a second minute ventilation threshold value. The first and second minute ventilation threshold values are used to determine a transition from an "awake" state of the patient to a "sleep" state of the patient. Due to the diurnal nature of the human wake-sleep cycle, the "predetermined period of time" in the step 306 is preferably at least 24 hours, and preferably a multiple of 24 hours, such that: (i) a first portion of the minute ventilation values received during the predetermined period of time are obtained when the patient is awake, (ii) a second portion of the minute ventilation values received during the predetermined period of time are obtained when the patient is asleep, and (iii) a ratio between the first portion and the second portion is representative of a wake-sleep cycle of the patient 108.

The first minute ventilation threshold value is greater than the second minute ventilation threshold value, and is used to screen the received minute ventilation value to determine if the carrying out of the remaining steps of the recurrent portion 304 is warranted. In calculating the first minute ventilation threshold value, a median value of the minute ventilation values received during the predetermined period of time is determined. The first minute ventilation threshold value is set to half the median value. The median value is substantially the "middle" minute ventilation value. That is, a number of the minute ventilation values received during the predetermined period of time are greater than the median value, and a substantially equal number of the minute ventilation values are less than the median value.

For example, during the step 306, the CPU 204 (FIG. 2) of the pacemaker 102 (FIGS. 1 and 2) may receive minute ventilation values from the minute ventilation sensing circuit 210 (FIG. 2) at 2-second intervals over a 24-hour period of time. Each time the CPU 204 receives a minute ventilation value, the CPU 204 may store the minute ventilation value in the memory 206 (FIG. 2). At the end of the 24-hour period of time, the CPU 204 may access the minute ventilation values stored in the memory 206, determine a median value of the minute ventilation values, and set the first minute ventilation threshold value to half the median value.

Alternately, the CPU 204 (FIG. 2) of the pacemaker 102 (FIGS. 1–2) may form a histogram of received minute ventilation values within the memory 206 (FIG. 2), and use the histogram to estimate the median value of the minute ventilation values. A range of expected minute ventilation values may be divided into equally-sized sub-ranges or "bins," and different memory locations of the memory 206 may be allocated for each of the bins. Each time the CPU 204 receives a minute ventilation value, the CPU 204 may determine which bin the minute ventilation value corresponds to, and add '1' to a running count maintained in the memory location allocated for that bin. At the end of the predetermined period of time (e.g., 24 hours), the CPU 204 may access the memory locations allocated for the bins, locate a bin wherein a number counts in bins above and below the bin are substantially equal, and select the median value within the sub-range of minute ventilation values represented by the bin. The CPU 204 may then set the first minute ventilation threshold value to half the selected median value.

Regarding the determining of the second minute ventilation value, the CPU 204 FIG. 2) of the pacemaker 102 (FIGS. 1–2) may keep a running estimate of a mean value (i.e., an average value) of the received minute ventilation values. The mean value represents a "central tendency" of the received minute ventilation values. At the end of a predetermined time interval (i.e., after receiving a predetermined number of minute ventilation values), the CPU 204 may calculate a measure of deviation of the minute ventilation values received during the time interval from a "current" estimate of the mean value. The CPU 204 may form a histogram of the deviations of the minute ventilation values from the mean value.

As further described below, a histogram of deviations of minute ventilation values from a mean value, formed over a "sleep-wake" cycle of the patient, has a first peak representing deviations of minute ventilation values from the mean value when the patient is asleep, a second peak representing deviations of minute ventilation values from the mean value when the patient is awake, and a "trough" between the first and second peaks representing deviations of minute ventilation values from the mean value when the patient is transitioning between the "awake" state and the "sleep" state. The CPU 204 may select a value for the second minute ventilation threshold value between the first and second peaks of the histogram.

For example, the CPU 204 (FIG. 2) may calculate a standard deviation of minute ventilation values received during predetermined time intervals (i.e., time "windows"), and may form a histogram of resulting minute ventilation standard deviation values within the memory 206 (FIG. 2). A range of expected minute ventilation standard deviation values may be divided into equally-sized sub-ranges or "bins," and different memory locations of the memory 206 may be allocated for each of the bins. At the end of each time window, the CPU 204 may calculate the minute ventilation standard deviation value, determine which bin the minute ventilation standard deviation value corresponds to, and add '1' to a running count maintained in the memory location allocated for that bin. At the end of the predetermined period of time (e.g., 24 hours), the CPU 204 may access the memory locations allocated for the bins. The CPU 204 may locate a bin having a lowest count between two other bins having the highest counts. The two bins having the highest counts include a bin of the first peak and a bin of the second peak, and the bin having the lowest count in between the first and second peaks is a bin of the trough of the histogram.

As further described below, the CPU 204 may select the second minute ventilation threshold value as a value (e.g., a minimum value) within the sub-range of minute ventilation values represented by the bin having the lowest count. Alternately, the CPU 204 may select the second minute ventilation threshold value as a value (e.g., a minimum value) within a sub-range of minute ventilation values represented by a bin between the bin having the lowest count and the bin of the first peak having one of the two highest count. Further, The CPU 204 may select the second minute ventilation threshold value as a value (e.g., a minimum value) within a sub-range of minute ventilation values represented by a bin midway between the bins of the first and second peaks and having the two highest counts.

As described above, at least some of the steps of the recurrent portion 304 are carried out at predetermined time intervals. During a step 310 of the recurrent portion 304, a minute ventilation value is received during one of the predetermined time intervals. The minute ventilation value is used to calculate an "MV Stdev Short" value and an "MV Stdev Long" value. The "MV Stdev Short" value is a standard deviation of minute ventilation values received during m time intervals including the current time interval and an immediately preceding m−1 time intervals. The "MV Stdev Long" value is a standard deviation of minute ventilation values received during n time intervals including the current time interval and the immediately preceding n−1 time intervals. In general, n≧m; however, for improved performance, n is preferably greater than m. For example, the value of m may be selected such that the "MV Stdev Short" value is calculated over a 2–5 minute period of time, and the value of n may be selected such that the "MV Stdev Long" value is calculated over a 10–15 minute period of time.

As described above, the minute ventilation sensing circuit 210 (FIG. 2) may produce a new minute ventilation value at the end of predetermined time intervals (e.g., 2-second time intervals). The CPU 204 (FIG. 2) may keep a running estimates of mean values (i.e., average values) of minute ventilation values received during various predetermined periods of time or time "windows." The CPU 204 may update the running estimates of the mean values each time a new minute ventilation value is produced by the minute ventilation sensing circuit 210 using:

$$\text{Mean}(i) = MV(i)/p + \text{Mean}(i-1) - \text{Mean}(i-1)/p$$

where Mean(i) is the mean value estimate during an ith time interval, MV(i) is the minute ventilation value produced the minute ventilation sensing circuit 210 during the ith time interval, p is the total number of elapsed time intervals, and Mean(i−1) is the mean value estimate during the time interval immediately preceding the ith time interval.

Regarding calculation of the "MV Stdev Short" value during a "current" time interval k, a mean value estimate Mean(k) value may be calculated using the minute ventilation values received during the current time interval and an immediately preceding m−1 time intervals (i.e., p=m), and the "MV Stdev Short" value may be calculated using:

$$\text{MVStdevShort} = \sqrt{\frac{\sum_{j=1}^{m}(MV(k-m-j) - \text{Mean}(k))^2}{m}}$$

Regarding calculation of the "MV Stdev Long" value during a "current" time interval k, a mean value estimate Mean(k) value may be calculated using the minute ventilation values received during the current time interval and an immediately preceding n−1 time intervals (i.e., p=n), and the "MV Stdev Long" value may be calculated using:

$$\text{MVStdevlong} = \sqrt{\frac{\sum_{j=1}^{n}(MV(k-n-j) - \text{Mean}(k))^2}{n}}$$

For example, the CPU 204 (FIG. 2) of the pacemaker 102 (FIGS. 1–2) may receive minute ventilation values at 2-second time intervals, and memory locations of the memory 206 (FIG. 2) may be allocated for minute ventilation values obtained during the immediately preceding n−1 2-second time intervals. During the step 312, the CPU 204 (FIG. 2) of the pacemaker 102 (FIGS. 1–2) may receive a "current" minute ventilation value, and access the memory locations allocated for the minute ventilation values obtained during the immediately preceding n−1 2-second time intervals. The CPU 204 may use the "current" minute ventilation value and the minute ventilation values obtained over the immediately preceding m−1 time intervals to compute the "MV Stdev Short" value. The CPU 204 may also use the "current" minute ventilation value and the minute ventilation values obtained over the immediately preceding n−1 time intervals to compute the "MV Stdev Long" value.

During a decision step 314, the "MV Stdev Long" value is compared to the first minute ventilation threshold value determined during the step 308. If the "MV Stdev Long" value is less than the first minute ventilation threshold value, an optional step 316 may be accomplished. On the other hand, if the "MV Stdev Long" value is greater than or equal to the first minute ventilation threshold value, a step 336 is accomplished. During the step 336, an "elapsed time" value is set to zero, and the recurrent portion 304 of the method 300 is exited.

Steps 316–320 represent an optional "activity cross-check" section of the recurrent portion 304 of the method 300. Steps 316–320 are believed to enhance performance of the method 300, but need not be accomplished for method 300 to work. During the optional step 316, an "activity value" is received during the predetermined time interval, wherein the activity value is indicative of a degree of movement of the patient during the predetermined time interval.

For example, the CPU 204 (FIG. 2) of the pacemaker 102 (FIGS. 1 and 2) may receive activity values from the activity sensing circuit 212 (FIG. 2) at 2-second intervals. The activity sensing circuit 212 may include and accelerometer, a bandpass filter, comparison circuitry, summing circuitry, and a register. An output signal of the accelerometer may be passed through the bandpass filter, and the resultant filtered output signal provided to the comparison circuitry. The comparison circuitry may compare the filtered output signal to a threshold value (e.g., a programmable threshold value). Peaks in the filtered output signal, which exceed the threshold value, are referred to herein as "activity counts." The summing circuitry may sum the "activity counts" occurring within a 2-second time interval in the register. At the end of each 2-second time interval, the activity sensing circuit 212 may provide the digital sum of the "activity counts" contained in the register, constituting the "activity value," and the register may be cleared.

During the optional step 318, the activity value is used to calculate an "ActThreshold" value, wherein the "ActThreshold" value is a sum of all "activity values" obtained during q time intervals including the current time interval and an immediately preceding q−1 time intervals. The value of q may be, for example, 20. The "ActThreshold" value during a "current' time interval k may be expressed as:

$$\text{ActThreshold} = \sum_{j=1}^{q} MV(k - q - j)$$

where MV(i) is the minute ventilation value produced the minute ventilation sensing circuit 210 during the ith time interval.

During the optional decision step 320, the activity value and the "ActThreshold" value calculated during the step 318 are compared. If the activity value is less than the "ActThreshold" value, an optional step 322 may be accomplished. On the other hand, if the activity value is greater than or equal to the "ActThreshold" value, the step 336 is accomplished. As described above, during the step 336, the "elapsed time" value is set to zero, and the recurrent portion 304 of the method 300 is exited.

Steps 322–324 represent an optional "time-of-day cross-check" section of the recurrent portion 304 of the method 300. Steps 322–324 are believed to enhance performance of the method 300, but need not be accomplished for method 300 to work. During the optional step 322, a "TimeofDay" value is obtained, wherein the "TimeofDay" value is indicative of a current time of day. During the optional decision step 324, the "TimeofDay" value is compared to a predetermined "ExpectedSleepTime" value, wherein the "ExpectedSleepTime" value is indicative of a time of day the patient is expected to go to sleep each day. The "ExpectedSleepTime" value may be, for example, a programmable value. If the "TimeofDay" value is greater than or equal to the "ExpectedSleepTime" value, an optional step 322 may be accomplished accomplished. On the other hand, if the "TimeofDay" value is less than the "ExpectedSleepTime" value, the step 336 is accomplished. As described above, during the step 336, the "elapsed time" value is set to zero, and the recurrent portion 304 of the method 300 is exited.

During a step 326, a length of the predetermined time interval is added to the "Elapsed Time" value. The "Elapsed Time" value is compared to an "ExpectedSleepTransitionTime" value during a decision step 328, wherein the "ExpectedSleepTransitionTime" value is a period of time allotted for the patient to transition from the "awake" state to the "sleep" state. The "ExpectedSleepTime" value may be, for example, a programmable value. If the "Elapsed Time" value is greater than or equal to the "ExpectedSleepTransitionTime" value, a decision step 330 is accomplished. On the other hand, if the "Elapsed Time" value is less than the "ExpectedSleepTransitionTime" value, the step 336 is accomplished. As described above, during the step 336, the "elapsed time" value is set to zero, and the recurrent portion 304 of the method 300 is exited.

During the decision step 330, the "MV Stdev Long" value is compared to the "MV Stdev Short" value. If the "MV Stdev Long" value is greater than or equal to the "MV Stdev Short" value, a decision step 332 is accomplished. On the other hand, if the "MV Stdev Long" value is less than the "MV Stdev Short" value, the step 336 is accomplished.

The decision step 330 enhances the method 300 by detecting abrupt transitions from the "sleep" state to the "awake" state. Typically, as the patient transitions from the "awake" state to the "sleep" state, the patient's minute ventilation decreases monotonically over time. Thus while the patient is sleeping, the "MV Stdev Long" value is typically greater than or equal to the "MV Stdev Short" value. However, when the patient wakes up abruptly and becomes active, the "MV Stdev Short" value will become greater than the "MV Stdev Long" value, indicating the patient has transitioned from the "sleep" state to the "awake" state.

During the decision step 332, the "MV Stdev Long" value and the second minute ventilation threshold value, calculated during the step 308, are compared. If the "MV Stdev Long" value is less than the second minute ventilation threshold value, a step 334 is accomplished. On the other hand, if the "MV Stdev Long" value is greater than or equal to the second minute ventilation threshold value, the step 336 is accomplished. As described above, during the step 336, the "elapsed time" value is set to zero, and the recurrent portion 304 of the method 300 is exited. During the step 334, the patient is determined to have transitioned from the "awake" state to the "sleep" state.

Figure 4:
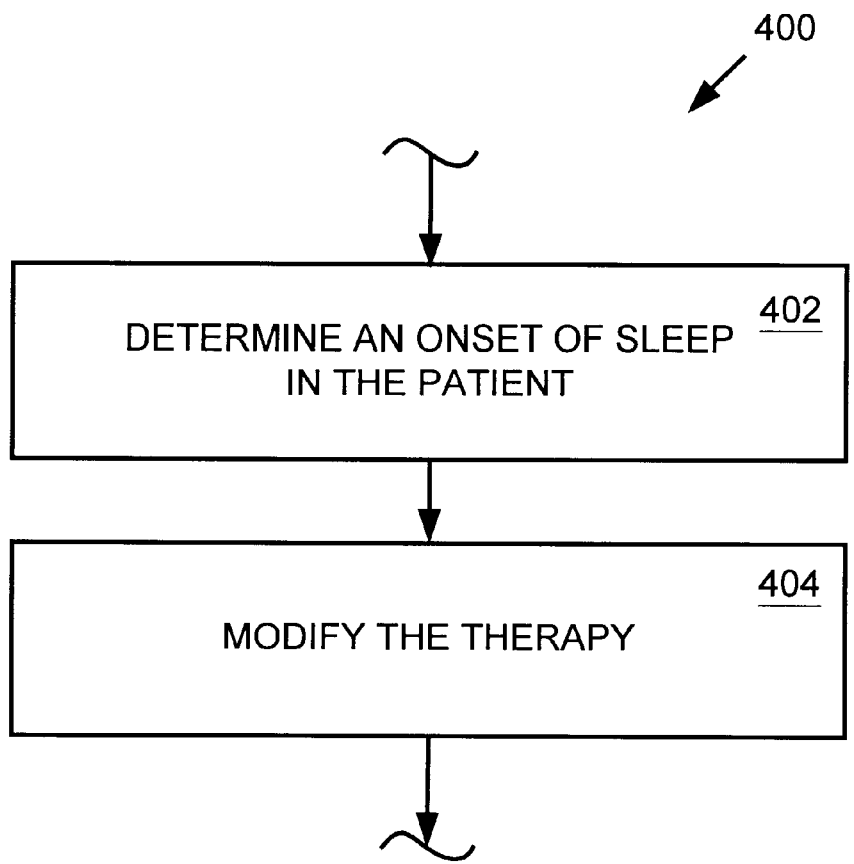
FIG. 4 is a flow chart of one embodiment of a method for providing a therapy to the patient, wherein the method involves determining an onset of sleep in the patient.

FIG. 4 is a flow chart of one embodiment of a method 400 for providing a therapy to a patient (e.g., the patient 108 of FIG. 1). The method 400 may be embodied within software residing in the memory 206 (FIG. 2) of the pacemaker 102 (FIGS. 1–2). The CPU 204 (FIG. 2) may carry out the method 400 when executing the software embodying the method 400. During a first step 402 of the method 400, an onset of sleep is determined in the patient. The step 402 of the method 400 may be accomplished by carrying out the steps of the method 300 of FIGS. 3A–3D. During a step 404, the therapy provided to the patient is modified.

For example, in the embodiment of FIG. 1, the patient 108 has the pacemaker 102 implanted therein, and the atrial lead 104 and the ventricular lead 106 extend from the pacemaker 102 and into the heart 110 of the patient 108. In the embodiment of FIG. 2, the pacemaker 102 includes the pacing output circuitry 202, the CPU 204, and the timing/pacing control circuitry 208. The pacing output circuitry 202 produces atrial and ventricular pacing pulses for stimulating the heart 110. The CPU 204 may store programmable "demand" mode, "low rate limit," and "AV interval" values in one or more registers of the timing/pacing control circuitry 208.

The timing/pacing control circuitry 208 includes sensing circuitry that receives and detects intrinsic electrical signals present within the heart 110 of the patient 108. Specifically, the sensing circuitry of the timing/pacing control circuitry 208 receives a first electrical signal indicative of an intrinsic contraction of the right atrium via the atrial lead 104. In response the first electrical signal, the sensing circuitry may generate an "atrial beat" signal within the timing/pacing control circuitry 208.

If the "demand" mode of the pacemaker 102 is enabled, the timing/pacing control circuitry 208 may provide an "atrial trigger" signal to the pacing output circuitry 202 if a frequency at which the "atrial beat" signals are generated is below the programmed "low rate limit." In other words, the timing/pacing control circuitry 208 may provide an "atrial trigger" signal to the pacing output circuitry 202 if the intrinsic beat rate of the heart 110 falls below the programmed "low rate limit." In response to the atrial trigger signal, the pacing output circuitry 202 may produce an atrial pacing pulse, and provide the atrial pacing pulse to the right atrium of the heart 110 via the atrial lead 104.

The CPU 204 may embody the above described method 300 for detecting onsets of sleep in the patient 108, and/or the method 400 for providing a therapy to a patient. For example, having detected an onset of sleep in the patient 108 (e.g., during the step 334 of the method 300), the CPU 204 may reduce the "low rate limit" value stored in the timing/pacing control circuitry 208 from a normal "resting rate" value (e.g., 60 beats per minute) to a "sleep rate" value, wherein the "sleep rate" value is less than or equal to the "resting rate." The "sleep rate" value may be, for example, a programmable value. The "sleep rate" value may be, for example, between 50 beats per minute and 60 beats per minute.

The above described methods 300 and 400 may also be useful for other purposes than reducing "low rate limit" values from normal "resting rate" values to "sleep rate" values in pacemakers. For example, the method 300 may be used to detect onsets of sleep for monitoring sleep-related events (i.e. sleep apnea, etc.), and the method 400 may be used in providing other medical therapies (e.g., electrical shocks for treating atrial fibrillation, administration of medications, etc.).

Figure 5A:
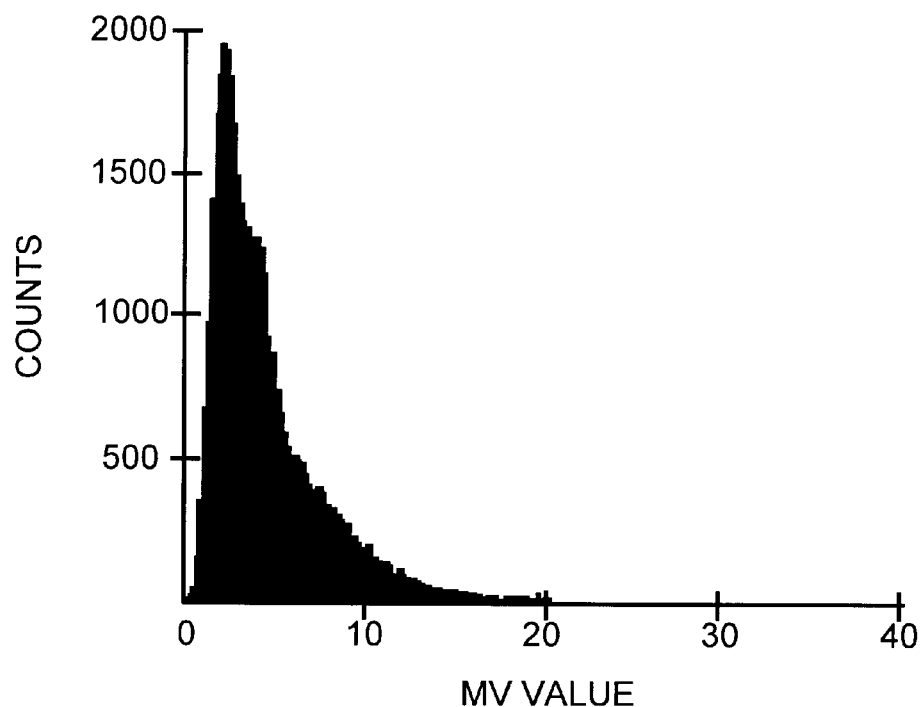
FIG. 5A is a histogram of minute ventilation values of a patient obtained via minute ventilation sensing circuitry over a 24-hour period.
Figure 5B:
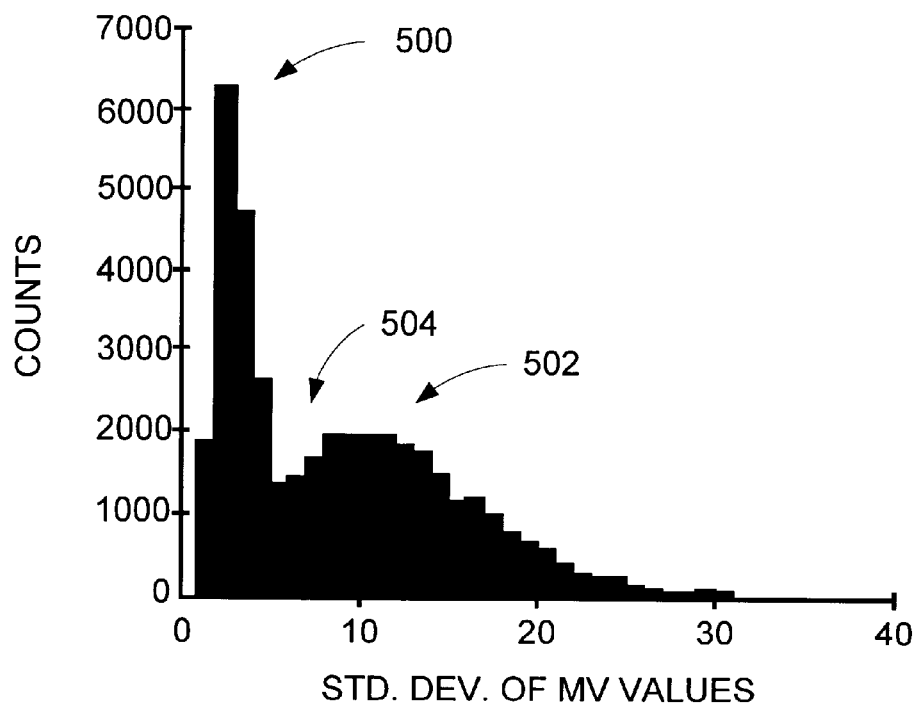
FIG. 5B is a histogram of standard deviations of the minute ventilation values used to form the histogram of FIG. 4A and received within 1-minute time windows.

FIGS. 5A and 5B will now be used to further describe the calculation of the second minute ventilation threshold value. FIG. 5A is a histogram of minute ventilation values of a patient obtained via minute ventilation sensing circuitry over a 24-hour period. In obtaining data for the histogram of FIG. 5A, minute ventilation sensing circuitry delivered current pulses at a rate of 16 Hz, thereby defining pulse "cycles" having "cycle times" of $\frac{1}{16}$ or 0.0625 seconds. The minute ventilation sensing circuitry converted an analog difference voltage between a "current" value of a thoracic impedance signal, obtained during a "current" pulse cycle, and a "previous" value of the thoracic impedance signal, obtained during a pulse cycle immediately preceding the current pulse cycle, to a digital "count" value. The minute ventilation sensing circuitry summed 32 of the digital "count" values produced by the analog-to-digital conversion circuitry in a register over predefined 2-second time intervals. At the end of each 2-second time interval, the minute ventilation sensing circuitry produced a "minute ventilation value" contained in the register, and the register is cleared.

A range of expected minute ventilation values was divided into equally-sized sub-ranges or "bins," and different memory locations of a memory were allocated for each of the bins. Each time a minute ventilation value was produced by the minute ventilation sensing circuitry, a determination was made as to which bin the minute ventilation value corresponds to, and a '1' was added to a running count maintained in the memory location allocated for that bin. At the end of the 24-hour period, the running counts maintained in the memory locations allocated for the bins were read out.

FIG. 5B is a histogram of standard deviations of the minute ventilation values used to form the histogram of FIG. 5A and received within 1-minute time windows. As described above, the minute ventilation sensing circuitry produced a new minute ventilation value at the end of each 2-second time interval. A running estimate of a mean of the minute ventilation values was updated each time a new minute ventilation value was produced by the minute ventilation sensing circuitry as described above. At the end of each 1-minute time window, ending with a 2-second time interval k, a mean value estimate Mean(k) was calculated using the minute ventilation values received during the current time interval and an immediately preceding 29 time intervals (i.e., p=30) as described above, and the standard deviation of the 30 minute ventilation values received during the time window was calculated using:

$$MVStdev = \sqrt{\frac{\sum_{j=1}^{30} (MV(k-30-j) - \text{Mean}(k))^2}{30}}$$

The histogram of FIG. 5B was formed within a memory. A range of expected minute ventilation standard deviation values was divided into equally-sized sub-ranges or "bins," and different memory locations of the memory were allocated for each of the bins. At the end of each 1-minute time window, the corresponding minute ventilation standard deviation value was calculated. A determination was made as to which bin the minute ventilation standard deviation value corresponded to, and '1' was added to a running count maintained in the memory location allocated for that bin. At the end of the 24-hour time period, the contents of the memory locations allocated for the bins were read out.

The histogram of FIG. 5B has a first peak 500, a second peak 502, and "trough" 504 located between the first peak 502 and the second peak 504. The first peak 500 represents a portion of the minute ventilation values produced by the minute ventilation sensing circuit 210 when the patient is asleep. The second peak 502 represents a different portion of the minute ventilation values produced by the minute ventilation sensing circuit 210 when the patient is awake.

Regarding use of the histogram of FIG. 5B to determine the second minute ventilation threshold value, the second minute ventilation threshold value may be selected from among the minute ventilation values located in the trough 504. For example, the second minute ventilation threshold value may be selected as a value (e.g., a minimum value) within the sub-range of minute ventilation values represented by the bin having the lowest count (i.e., a bin having the lowest count within the trough 504). Alternately, the second minute ventilation threshold value may be selected as a value (e.g., a minimum value) within a sub-range of minute ventilation values represented by a bin between the bin having the lowest count within the trough 504 and a bin of the first peak 500 having the highest count. Further, the second minute ventilation threshold value may be selected as a value (e.g., a minimum value) within a sub-range of minute ventilation values represented by a bin midway between a bin of the first peak 500 having a highest count, and a bin of the second peak 502 having a highest count.

Figure 6:
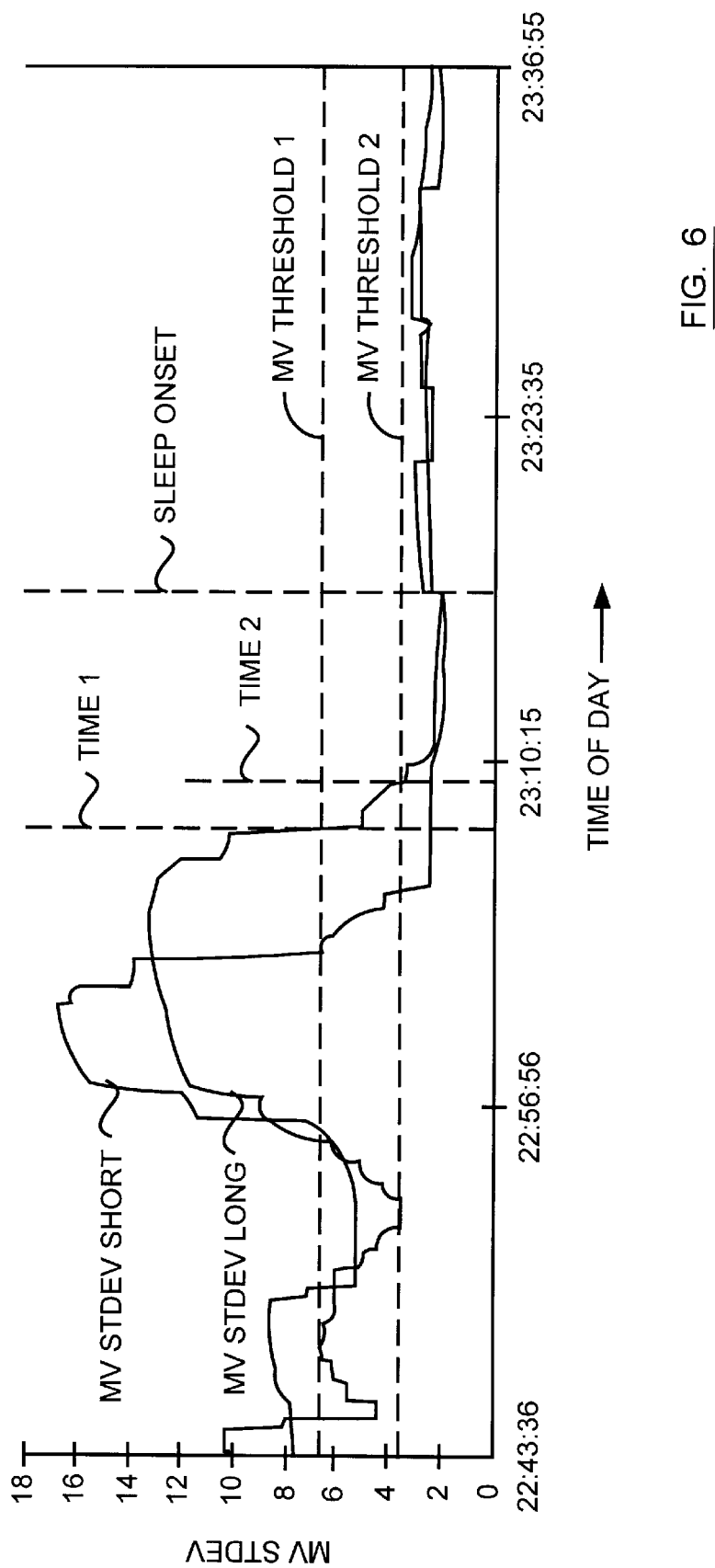
FIG. 6 is a graph of standard deviation values "MV Stdev Long" and "MV Stdev Short" calculated using minute ventilation values produced during 2-second time intervals and indicative of the minute ventilation of a patient.

FIG. 6 is a graph of "MV Stdev Long" and "MV Stdev Short" values described above, wherein the "MV Stdev Long" and "MV Stdev Short" values were calculated using minute ventilation values produced during 2-second time intervals and indicative of the minute ventilation of a patient. In FIG. 6, the first minute ventilation threshold value described above defines an "MV Threshold 1" level, and the second minute ventilation threshold value described above defines an "MV Threshold 2" level. As illustrated in FIG. 6, the "MV Threshold 1" level is greater than the "MV Threshold 2" level. As described above, the first minute ventilation threshold value is used to screen a received minute ventilation value to determine if the received minute ventilation value is sufficiently low as to warrant further analysis to detect an onset of sleep.

A time of day labeled "Sleep Onset" in FIG. 6 is a time the method 300 of FIGS. 3A–3D determine an onset of sleep in the patient. Prior to the "Sleep Onset" time, the "MV Stdev Short" and "MV Stdev Long" values drop below the "MV Threshold 1" level several times, and occasionally drop below the "MV Threshold 2" level, indicating a decrease in patient activity and an impending transition from an "awake" state to a "sleep" state. At a time of day labeled "Time 1" in FIG. 6, prior to the "Sleep Onset" time, the "MV Stdev Long" value drops below the "MV Threshold 1" level, thus indicating received minute ventilation values are sufficiently low as to warrant further analysis to detect an onset of sleep. (See the step 314 of the method 300, FIG. 3A.) At a time of day labeled "Time 2" in FIG. 6, between the "Time 1" and "Sleep Onset" times, the "MV Stdev Long" value drops below the "MV Threshold 2" level, and remains below the "MV Threshold 2" level for all subsequent times of day. The "Sleep Onset" time occurs a period of time after "Time 2" equal to the "ExpectedSleepTransitionTime" described above. (See the step 328 of the method 300, FIG. 3D.)

Figure 7:
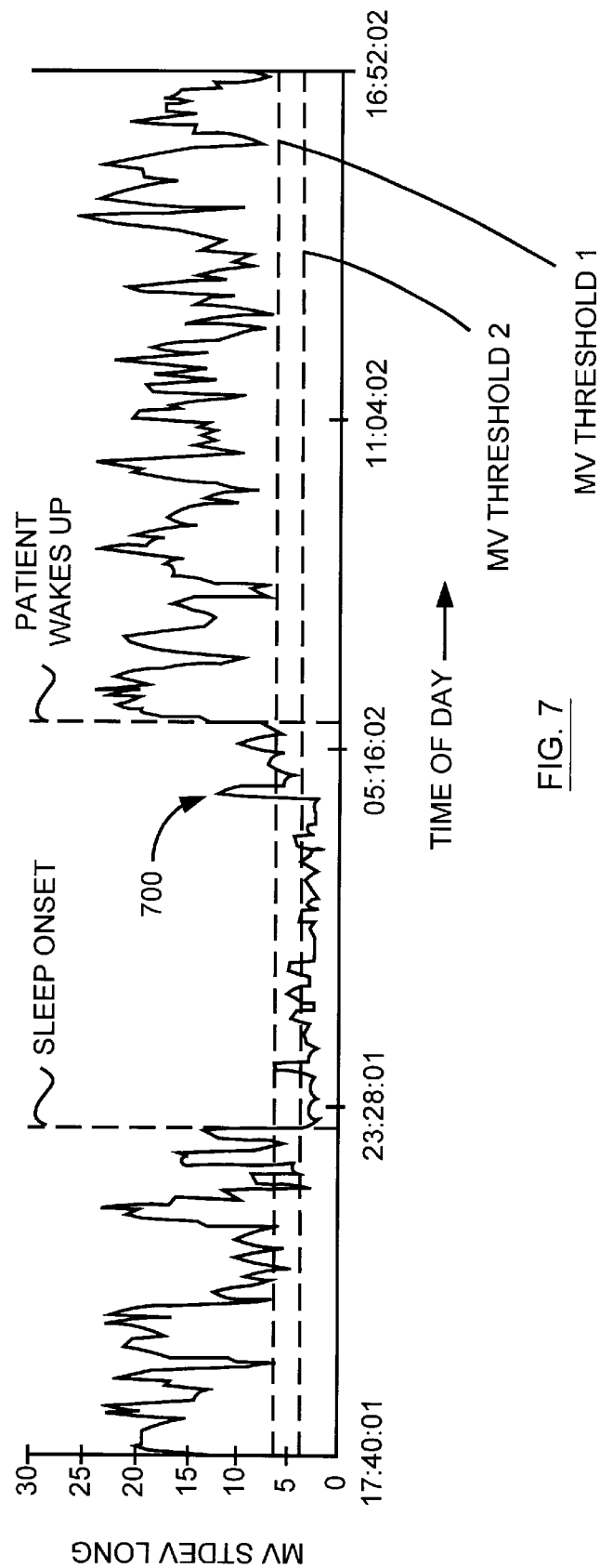
FIG. 7 is a graph of a standard deviation value "MV Stdev Long" calculated using minute ventilation values produced during 2-second time intervals and indicative of the minute ventilation of a patient.

FIG. 7 is a graph of "MV Stdev Long" values described above, wherein the "MV Stdev Long" values were calculated using minute ventilation values produced during 2-second time intervals and indicative of the minute ventilation of a patient. As in FIG. 6, the first minute ventilation threshold value described above defines a level labeled "MV Threshold 1," and the second minute ventilation threshold value described above defines a level labeled "MV Threshold 2."

A time of day labeled "Sleep Onset" in FIG. 7 is a time the method 300 of FIGS. 3A–3D determine an onset of sleep in the patient. Prior to the "Sleep Onset" time, the "MV Stdev Long" value substantially remains above the "MV Threshold 1" and "MV Threshold 2" levels, indicating a relatively high level of patient activity characteristic of an "awake" state of the patient. Just prior to the "Sleep Onset" time, the "MV Stdev Long" value drops below the "MV Threshold 1" level several times, and occasionally drops below the "MV Threshold 2" level, indicating a decrease in patient activity and an impending transition from the "awake" state to a "sleep" state. At the "Sleep Onset" time, the "MV Stdev Long" value has dropped below the "MV Threshold 2" level for a period of time equal to the "ExpectedSleepTransitionTime" described above. (See the step 328 of the method 300, FIG. 3D.)

The patient woke up at a time of day labeled "Patient Wakes Up" in FIG. 7. At various times between the "Sleep Onset" time and the time labeled "Patient Wakes Up" in FIG. 7, the "MV Stdev Long" value rises above the "MV Threshold 2" level, but does not rise above the "MV Threshold 1" level. A peak 700 in the "MV Stdev Long" value, exceeding the "MV Threshold 1" level, occurs around a time the patient got out of bed briefly. Between a time of day corresponding to the peak 700 and the time labeled "Patient Wakes Up" in FIG. 7, the "MV Stdev Long" value is above the "MV Threshold 2" level, and occasionally rises briefly above the "MV Threshold 1" level, indicating an increase in patient activity and an impending transition from the "sleep" state to the "awake" state. Subsequent to the time labeled "Patient Wakes Up" in FIG. 7, the "MV Stdev Long" value remains above the "MV Threshold 1" and "MV Threshold 2" levels, indicating a relatively high level of patient activity characteristic of the "awake" state of the patient.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An implantable medical device for implantation in a patient, comprising:
   a therapy component configured to provide a therapy to the patient;
   a minute ventilation sensing circuit configured to produce minute ventilation values indicative of a minute ventilation of the patient at time intervals; and
   computational circuitry coupled to the therapy component and the minute ventilation sensing circuit and configured to receive a plurality of the minute ventilation values at predetermined time intervals over a period of time, to generate a first threshold and a second threshold corresponding to a physiologic transition of the patient between a first state and a second state, to generate a first distribution late of minute ventilation values of the plurality of minute ventilation values received during first time intervals of the predetermined time intervals including a first current time interval m and first preceding time intervals m-1 and a second distribution rate of minute ventilation values of the plurality of minute ventilation values received during second time intervals of the predetermined time intervals including a second time interval n and a second preceding time intervals n-1, to detect onset of the second state in response to the second distribution rate being less than the first threshold, an abrupt transition between the first state and the second state, and the second distribution rate being greater than or equal to the first distribution rate, and to signal the therapy component to modify the therapy when the onset of the second state is detected in the patient.

2. The implantable medical device of claim 1, wherein the first threshold corresponds to one halt of a median of the plurality of minute ventilation values over the period of time.

3. The implantable medical device of claim 1, wherein the second threshold corresponds to a mean of the plurality of minute ventilation values aver the period of time.

4. The implantable medical device of claim 1, wherein the first threshold is greater than the second threshold.

5. The implantable medical device of claim 1, wherein n is greater than m.

6. The implantable medical device of claim 5, wherein m is selected such that the first distribution rate is generated over approximately a 2–5 minute period of time and n is selected such that the second distribution rate is generated over approximately a 10–15 minute period of time.

7. The implantable medical device of claim 1, further comprising an activity sensor coupled to the computational circuitry and configured to generate activity values indicative of a level of activity of the patient, wherein the computational circuitry detects onset of the second state in response to the activity values.

8. The implantable medical device of claim 1, wherein the computational circuitry includes a timing/pacing control circuit to generate time of day information, and wherein the computational circuitry detects onset of the second stage in response to the time of day information corresponding to the second state.

9. The implantable medical device of claim 8, wherein the computational circuitry detects the onset of the second stage in response to an amount of time, corresponding to the second distribution rate being less than the first threshold, being less than a predetermined transition time threshold.

10. The implantable medical device of claim 1, wherein the computational circuitry detects the onset of the second stage in, response to the second distribution rate being less than the second threshold.

11. The implantable medical device of claim 1, wherein the first state corresponds to the patient being awake and the second state corresponds to the patient being asleep.

12. The implantable medical device of claim 1, wherein the modification of the therapy includes one of reducing a lower rate, monitoring sleep-related events, modifying electrical shocks for treating atrial fibrillation, and modifying administration of medications.

13. The implantable medical device of claim 1, wherein the means for detecting detects the onset of the second stage in response to the second distribution rate being less than the second threshold.

14. The implantable medical device of claim 1, wherein the modifying includes one of reducing a lower rate, monitoring sleep-related events, modifying electrical shocks for treating atrial fibrillation, and modifying administration of medications.

15. An implantable medical device for implantation in a patient, comprising:
a therapy component configured to provide a therapy to the patient;
a minute ventilation sensing circuit configured to produce minute ventilation values indicative of a minute ventilation of the patient at time intervals;
an activity sensor configured to generate activity values indicative of a level of activity of the patient;
a timing/pacing control circuit to generate time of day information; and
computational circuitry coupled to the therapy component and the minute ventilation sensing circuit and configured to receive a plurality of the minute ventilation values at predetermined time intervals over a period of time to generate a first threshold and a second threshold corresponding to a physiologic transition of the patient between a first state and a second state, to generate a first distribution rate of minute ventilation values of the plurality of minute ventilation values received during first time intervals of the predetermined time intervals Including a first current time interval m and first preceding time intervals m-1 and a second distribution rate of minute ventilation values of the plurality of minute ventilation values received during second time intervals of the predetermined time intervals including a second time Interval n and second preceding time intervals n-1, to detect onset of the second state In response to the second distribution rate being less than the first threshold, the activity levels, the time of day information corresponding to the second state, an abrupt transition between the first state and the second state, and the second distribution rate being greater than or equal to the first distribution rate, and to signal the therapy component to modify the therapy when the onset of the second state is detected in the patient.

16. The implantable medical device of claim 15, wherein the first threshold corresponds to one half of a median of the plurality of minute ventilation values over the period of time.

17. The implantable medical device of claim 15, wherein the second threshold corresponds to a mean of the plurality of minute ventilation values over the period of time.

18. The implantable medical device of claim 15, wherein the first threshold is greater than the second threshold.

19. The implantable medical device of claim 15, wherein n is greater than m.

20. The implantable medical device of claim 19, wherein m is selected such that the first distribution rate is generated over approximately a 2–5 minute period of time and n is selected such that the second distribution rate is generated over approximately a 10–15 minute period of time.

21. The implantable medical device of claim 15, wherein the computational circuitry detects the onset of the second stage in response to an amount of time, corresponding to the second distribution rate being less than the first threshold, being less than a predetermined transItion time threshold.

22. The implantable medical device of claim 15, wherein the computational circuitry detects the onset of the second stage in response to the second distribution rate being less than the second threshold.

23. The implantable medical device of claim 15, wherein the first state corresponds to the patient being awake and the second state corresponds to the patient being asleep.

24. The implantable medical device of claim 15, wherein the modification of the therapy includes one of reducing a lower rate, monitoring sleep-related events, modifying electrical shocks for treating atrial fibrillation, and modifying administration of medications.

25. A method of providing therapy to a patient having an implantable medical device, comprising:
   sensing minute ventilation values indicative of a minute ventilation of the patient;
   generating a first threshold and a second threshold corresponding to a physiologic transition of the patient between a first state and a second state in response to the minute ventilation values;
   generating a first distribution rate of a plurality of the sensed minute ventilation values received during first time intervals of predetermined time intervals including a first current time interval m and first preceding time intervals m-1 and a second distribution rate of a plurality of the sensed minute ventilation values received during second time intervals of the predetermined time intervals including a second time interval n and second preceding time intervals n-1;
   detecting onset of the second state In response to the second distribution rate being less than the first threshold, an abrupt transition between the first state and the second state, and the second distribution rate being greater than or equal to the first distribution rate; and
   modifying the therapy in response to the detected onset of the second state.

26. The method of claim 25, wherein the first threshold corresponds to one half of a median of the plurality of minute ventilation values over the period of time.

27. The method of claim 25, wherein the second threshold corresponds to a mean of the plurality of minute ventilation values over the period of time.

28. The method of claim 25, wherein the first threshold is greater than the second threshold.

29. The method of claim 25, wherein n is greater than m.

30. The method of claim 29, wherein m is selected such that the first distribution rate is generated over approximately a 2–5 minute period of time and n is selected such that the second distribution rate is generated over approximately a 10–15 minute period of time.

31. The method of claim 25, further comprising generating activity values indicative of a level of activity of the patient, wherein the step of detecting includes detecting onset of the second state in response to the activity values.

32. The method of claim 25, further comprising generating time of day information, wherein the step of detecting includes detecting the onset of the second stage in response to the time of day information corresponding to the second state.

33. The method of claim 32, further comprising determining an amount of time corresponding to the second distribution rate being less than the first threshold, wherein the step of detecting includes detecting the onset of the second stage in response to the determined amount of time being less than a predetermined transition time threshold.

34. The method of claim 25, wherein the step of detecting includes detecting the onset of the second stage in response to the second distribution rate being less than the second threshold.

35. The method of claim 25, wherein the first state corresponds to the patient being awake and the second state corresponds to the patient being asleep.

36. The method of claim 25, wherein the step of modifying includes one of reducing a lower rate, monitoring sleep-related events, modifying electrical shocks for treating atrial fibrillation, and modifying administration of medications.

37. A method of providing therapy to a patient having an implantable medical device, comprising:
   sensing minute ventilation values indicative of a minute ventilation of the patient;
   generating activity values indicative of a level of activity of the patient;
   generating time of day information;
   generating a first threshold and a second threshold corresponding to a physiologic transition of the patient between a first state and a second state in response to the minute ventilation values;
   generating a first distribution rate of a plurality of the sensed minute ventilation values received during first time intervals of predetermined time intervals including a first current time interval m and first preceding time intervals m-1;
   generating a second distribution rate of minute ventilation values of the plurality of minute ventilation values received during second time intervals of the predetermined time intervals including a second time interval n and second preceding time intervals n-1;
   detecting onset of the second state in response to the second distribution rate being less than the first threshold, the activity levels, the time of day information corresponding to the second state, an abrupt transition between the first state and the second state, and the second distribution rate being greater than or equal to the first distribution rate; and
   modifying the therapy in response to the detected onset of the second state.

38. The method of claim 37, wherein the first threshold corresponds to one half of a median of the plurality of minute ventilation values over the period of time, the second threshold corresponds to a mean of the plurality of minute ventilation values over the period of time, and m is selected such that the first distribution rate is generated over approximately a 2–5 minute period of time and n is selected such that the second distribution rate is generated over approximately a 10–15 minute period of time.

39. The method of claim 38, further comprising determining an amount of time corresponding to the second distribution rate being less than the first threshold, wherein the step of detecting includes detecting the onset of the second stage in response to the determined amount of time being less than a predetermined transition time threshold.

40. The method of claim 39, wherein the step of detecting includes detecting the onset of the second stage in response to the second distribution rate being less than the second threshold.

41. The method of claim 40, wherein the first state corresponds to the patient being awake and the second state corresponds to the patient being asleep.

42. The method of claim 41, wherein the step of modifying includes one of reducing a lower rate, monitoring sleep-related events, modifying electrical shocks for treating atrial fibrillation, and modifying administration of medications.

43. An implantable medical device for implantation in a patient, comprising:

means for sensing minute ventilation values indicative of a minute ventilation of the patient;

means for generating a first threshold and a second threshold corresponding to a physiologic transition of the patient between a first state and a second state in response to the minute ventilation values;

means for generating a first distribution rate of a plurality of the sensed minute ventilation values received during first time intervals of predetermined time intervals including a first current time interval m and first preceding time intervals m-1 and a second distribution rate of a plurality of the sensed minute ventilation values received during second time intervals of the predetermined time intervals including a second time interval n and second preceding time intervals n-1;

means for detecting onset of the second state in response to the second distribution rate being less than the first threshold, an abrupt transition between the first state and the second state, and the second distribution rate being greater than or equal to the first distribution rate; and means for modifying the therapy in response to the detected onset of the second state.

44. The implantable medical device of claim 42, wherein the first threshold corresponds to one half of a median of the plurality of minute ventilation values over the period of time, the second threshold corresponds to a mean of the plurality of minute ventilation values over the period of time, the first threshold is greater than the second threshold, and m is selected such that the first distribution rate is generated over approximately a 2–5 minute period of time and n is selected such that the second distribution rate is generated over approximately a 10–15 minute period of time.

45. The implantable medical device of claim 43, further comprising means for generating activity values indicative of a level of activity of the patient, wherein the means for detecting detects onset of the second state in response to the activity values.

46. The implantable medical device of claim 43, further comprising means for generating time of day information, and wherein the means for detecting detects onset of the second stage in response to the time of day information corresponding to the second state.

47. The implantable medical device of claim 46, further comprising means for determining an amount of time corresponding to the second distribution rate being less than the first threshold, wherein the means for detecting detects the onset of the second stage in response to the determined amount of time being less than a predetermined transition time threshold.

48. The implantable medical device of claim 43, wherein the first state corresponds to the patient being awake and the second state corresponds to the patient being asleep.

* * * * *

UNITED STATES PATENT AND TRADEMARK OFFICE
CERTIFICATE OF CORRECTION

PATENT NO.        : 6,731,984 B2
APPLICATION NO. : 09/876528
DATED             : May 4, 2004
INVENTOR(S)       : Cho et al.

It is certified that error appears in the above-identified patent and that said Letters Patent is hereby corrected as shown below:

Col. 21, Line 2, after "distribution" delete "late" and insert --rate--.
Col. 21, Line 25, after "values" delete "aver" and insert --over--.
Col. 21, Line 54, after "second" delete "stage in, response" and
              insert --stage in response--.
Col 22, Line 28, after "intervals" delete "Including" and insert --including--
Col. 22, Line 33, after "time" delete "Interval" and insert --interval--.
Col. 22, Line 34, after "state" delete "In" and insert --in--.
Col. 22, Line 63, after "predetermined" delete "transltion time" to
              --transition time--.
Col. 23, Line 26, after "state" delete "In" and insert --in--.

Signed and Sealed this

Eighteenth Day of July, 2006

JON W. DUDAS
*Director of the United States Patent and Trademark Office*